(12) United States Patent
Boustany et al.

(10) Patent No.: US 7,129,043 B1
(45) Date of Patent: Oct. 31, 2006

(54) METHODS OF SCREENING FOR RISK OF PROLIFERATIVE DISEASE AND METHODS FOR THE TREATMENT OF PROLIFERATIVE DISEASE

(75) Inventors: Rose-Mary N. Boustany, Durham, NC (US); Wei-Xing Guo, Northridge, CA (US); Andrea Amalfitano, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/830,045

(22) PCT Filed: Oct. 21, 1999

(86) PCT No.: PCT/US99/24695

§ 371 (c)(1),
(2), (4) Date: Jan. 23, 2002

(87) PCT Pub. No.: WO00/23624

PCT Pub. Date: Apr. 27, 2000

Related U.S. Application Data

(60) Provisional application No. 60/105,262, filed on Oct. 22, 1998.

(51) Int. Cl.
C07H 21/04 (2006.01)
C12Q 1/68 (2006.01)
(52) U.S. Cl. .................. 435/6; 435/91.1; 435/91.2; 536/23.1; 536/24.3
(58) Field of Classification Search ............ 435/6, 435/91.1, 91.2; 536/23.1
See application file for complete search history.

(56) References Cited

U.S. PATENT DOCUMENTS

| | | | |
|---|---|---|---|
| 4,599,308 | A | 7/1986 | Hamer et al. |
| 4,797,368 | A | 1/1989 | Carter et al. |
| 5,139,941 | A | 8/1992 | Muzyczka et al. |
| 5,173,414 | A | 12/1992 | Lebkowski et al. |
| 5,176,996 | A | 1/1993 | Hogan et al. |
| 5,252,479 | A | 10/1993 | Srivastava |
| 5,288,514 | A | 2/1994 | Ellman |
| 5,354,678 | A | 10/1994 | Lebkowski et al. |
| 5,436,146 | A | 7/1995 | Shenk et al. |
| 5,445,934 | A | 8/1995 | Fodor et al. |
| 5,468,634 | A | 11/1995 | Liu |
| 5,474,935 | A | 12/1995 | Chatterjee et al. |
| 5,518,913 | A | 5/1996 | Massie et al. |
| 5,565,324 | A | 10/1996 | Still et al. |
| 5,585,269 | A | 12/1996 | Earp, III et al. |
| 5,585,362 | A | 12/1996 | Wilson et al. |
| 5,587,308 | A | 12/1996 | Carter et al. |
| 5,589,477 | A | 12/1996 | Chokai et al. |
| 5,604,090 | A | 2/1997 | Alexander et al. |
| 5,616,326 | A | 4/1997 | Spibey |
| 5,622,856 | A | 4/1997 | Natsoulis |
| 5,650,316 | A | 7/1997 | Aggarwal et al. |
| 5,658,776 | A | 8/1997 | Flotte et al. |
| 5,670,488 | A | 9/1997 | Gregory et al. |
| 5,677,158 | A | 10/1997 | Zhou et al. |
| 5,681,731 | A | 10/1997 | Lebkowski et al. |
| 5,707,865 | A | 1/1998 | Kohn et al. |
| 5,734,039 | A | 3/1998 | Calabretta et al. |
| 5,747,335 | A | 5/1998 | Haseloff et al. |
| 5,766,942 | A | 6/1998 | Haseloff et al. |
| 5,773,260 | A | 6/1998 | Goldberg et al. |
| 5,811,537 | A | 9/1998 | Griesen |
| 5,817,635 | A | 10/1998 | Eckstein et al. |

OTHER PUBLICATIONS

Rylova et al. "The CLN3 gene is a novel molecular target for cancer drug discovery." Cancer Research. vol. 62, pp. 801-808, Feb. 2002.*
Dermer, Gerald. "Another Anniversary for the war on cancer." Bio Technology, vol. 12, pp. 320, Mar. 1994.*
Chabert et al. "Cell culture of tumors alters endogenous poly(ADPR)polymerase expression and activity." Int. J. Cancer. vol. 53, pp. 837-842, 1993.*
Persaud-Swawin (Hum. Mol. Genetics. vol. 11, No. 18, pp. 2129-2142, 2002).*
Altschul, et al., *Basic Local Alignment Search Tool*, J. Mol. Biol., vol. 215, pp. 403-410 (1990.
Amarnath, et al., *Chemical Synthesis of Oligonucleotides*, Chemical Reviews, vol. 77, No. 2, pp. 193-217 (1977).
Andersson, et al., *Cloning, Structure, and Expression of the Mitochondrial Cytochrome P-450 Sterol 26-Hydroxylase, a Bile Acid Biosynthetic Enzyme*, Journal of Biological Chemistry, vol. 264, No. 14, pp. 8222-8229 (1989).
Arends, et al., *Apoptosis: The Role of the Endonuclease*, American Journal of Pathology, vol. 136, No. 3, pp. 593-608).
Atherton, et al., *The Solid Phase in Solid-Phase Synthesis*, Perspectives in Peptide Chemistry, pp. 101-117 (Karger, Basel 1981).
Bligh, et al., *A Rapid Method of Total Lipid Extraction and Purification*, Canadian Journal of Biochemistry and Physiology, vol. 37, No. 8, pp. 911-917 (Aug. 1959).
Boustany, et al., *Neurological Progress—The Neuronal Ceroid Lipofuscinoses: A Review*, Revue Neurologique, vol. 145, No. 2, pp. 105-110 (1989).
Boustany, Rose-Mary, *Neurology of the Neuronal Ceroid-Lipofuscinoses: Late Infantile and Juvenile Types*, American Journal of Medical Genetics, vol. 42, pp. 533-535 (1992).
Boustany, et al., *Clinical Classification of Neuronal Ceroid-Lipofuscinosis Subtypes*, American Journal of Medical Genetics Supplement, vol. 5, pp. 47-58 (1988).

(Continued)

Primary Examiner—Jeanine A. Goldberg
(74) Attorney, Agent, or Firm—Myers, Bigel, Sibley & Sajovec, P.A.

(57) ABSTRACT

A method of screening a subject for a proliferative disease risk factor comprises detecting the presence or absence of upregulation of the CLN3 gene in the subject. The upregulation of the CLN3 gene in the subject indicates the subject is at increased risk of developing a proliferative disease. Methods of screening compounds for the treatment of proliferative diseases based on the CLN3 gene and its product are also disclosed, along with methods of treating such diseases and vectors useful therefore.

7 Claims, 18 Drawing Sheets

OTHER PUBLICATIONS

Fieck, et al., *Modifications of the E. coli lac repressor for expression in eukaryotic cells: effects of nuclear signal sequences on protein activity and nuclear accumulation*, Nucleic Acids Research, vol. 20, No. 7, pp. 1785-1791 (Apr. 11, 1992).

Friedmann, Theodore, *Progress Toward Human Gene Therapy*, Science, vol. 244, pp. 1275-1281 (Jun. 16, 1989).

Fridkin, Mati, *Polymeric Reagents in Peptide Synthesis*, The Peptides, vol. 2, pp. 333-363 (1979).

Stoll, et al., *Effect of Vincristine on Sister Chromatid Exchanges of Normal Hyman Lymphocytes*, Cancer Research, vol. 36, pp. 2710-2713 (Aug. 1976).

Howard, et al., *Cell Cycle Arrest of Proliferating Neuronal Cells by Serum Deprivation Can Result in Either Apoptosis or Differentiation*, Journal of Neurochemistry, vol. 60, No. 5, pp. 1783-1791 (May 1993).

Kaufmann, et al., *Specific Proteolytic Cleavage of Poly(ADP-ribose) Polymerase: An Early Marker of Chemotherapy-induced Apoptosis*, Cancer Research, pp. 3976-3985 (Sep. 1, 1993).

Obeid, et al., *Programmed Cell Death Induced by Ceramide*, Science, vol. 259, pp. 1769-1771 (Mar. 19, 1993).

Perry, et al., *Bcl-2 acts upstream of the PARP protease and prevents it activation*, Cell Death and Differentiation, vol. 4, No. 1, pp. 29-33 (1997).

Rosenbaum, et al., *Evidence of Hypoxia-induced, Programmed Cell Death of Cultured Neurons*, Annals of Neurology, vol. 36, No. 6, pp. 864-870.

Walker, P. Roy, et al., *Topoisomerase II-reactive Chemotherapeutic Drugs Induce Apoptosis in Thymocytes*, Cancer Research, vol. 51, No. 4, pp. 1078-1085 (Feb. 15, 1991).

Woo, Savio L.C., *Adenovirus redirected*, Nature Biotechnology, vol. 14, No. 11, pp. 1538 (Nov. 1996).

Lee, et al., *Ceramide Inactivates Cellular Protein Kinase Cα\**, Journal of Biological Chemistry, vol. 271, No. 22, pp. 13169-13174 (Mary 31, 1996).

Zhang, et al., *Bcl-2 interrupts the ceramide-mediated pathway of cell death*, Proc. Natl. Acad. Sci. USA, vol. 93, pp. 5325-5328 (May 1996).

Bertrand, et al., *Induction of a Common Pathway of Apoptosis by Staurosporine*, Experimental Cell Research, vol. 211, pp. 314-321 (1994).

Boustany, R-M, et al., *Seizures, Depression and Dementia in Teenagers with Batten Disease*, J. Inher. Metab. Dis., vol. 16, pp. 252-255 (1993).

Griffith, et al., *Fas Ligand-Induced Apoptosis as a Mechanism of Immune Privilege*, Science, vol. 270, pp. 1189-1193 (Nov. 17, 1995).

Griffith, et al., *CD95-Induced Apoptosis of Lymphocytes in an Immune Privileged Site Induces Immunological Tolerance*, Immunity, vol. 5, pp. 7-16 (Jul. 1996).

Hannun, Yusuf A., *Functions of Ceramide in Coordinating Cellular Responses to Stress*, Science, vol. 274, pp. 1855-1859 (Dec. 13, 1996).

Janes, et al, *A model of Batten disease protein CLN3: Functional implications from homology and mutations*, Federation of European Biochemical Societies, vol. 399, pp. 75-77 (1996).

Kulkarni, et al,. *Serum deprivation induces apoptotic cell death in a subset of Balb/c 3T3 fibroblasts*, Journal of Cell Science, vol. 107, pp. 1169-1179 (1994).

Lane, et al., *Apoptosis as the Mechanism of Neurodegeneration in Batten's Disease*, Journal of Neurochemistry, vol. 67, No. 2, pp. 677-683 (1996).

Liu, et al., *Induction of Apoptotic Program in Cell-Free Extracts: Requirement for dATP and Cytochrome c*, Cell, vol. 86, pp. 147-157 (Jul. 12, 1996).

Mitchison, et al., *Genomic Structure and Complete Nucleotide Sequence of the Batten Disease Gene, CLN3*, Genomics, vol. 40, pp. 346-350 (1997).

Peña, et al., *Stress-Induced Apoptosis and the Sphingomyelin Pathway*, Biochemical Pharmacology, vol. 53, pp. 615-621 (1997).

Puranam, et al., *Upregulation of Bcl-2 and Elevation of Ceramide in Batten Disease*, Neuropediatrics, vol. 28, pp. 37-41 (1997).

Smyth, et al., *prICE: a downstream target for ceramide-induced apoptosis and for the inhibitory action of Bcl-2*, Biochem. J., vol. 316, pp. 25-28 (1996).

The International Batten Disease Consortium, *Isolation of a Novel Gene Underlying Batten Disease, CLN3*, Cell, vol. 82, pp. 949-957 (Sep. 22, 1995).

White, Eileen, *Life, death, and the pursuit of apoptosis*, Genes & Development, vol. 10, pp. 1-15 (1996).

\* cited by examiner

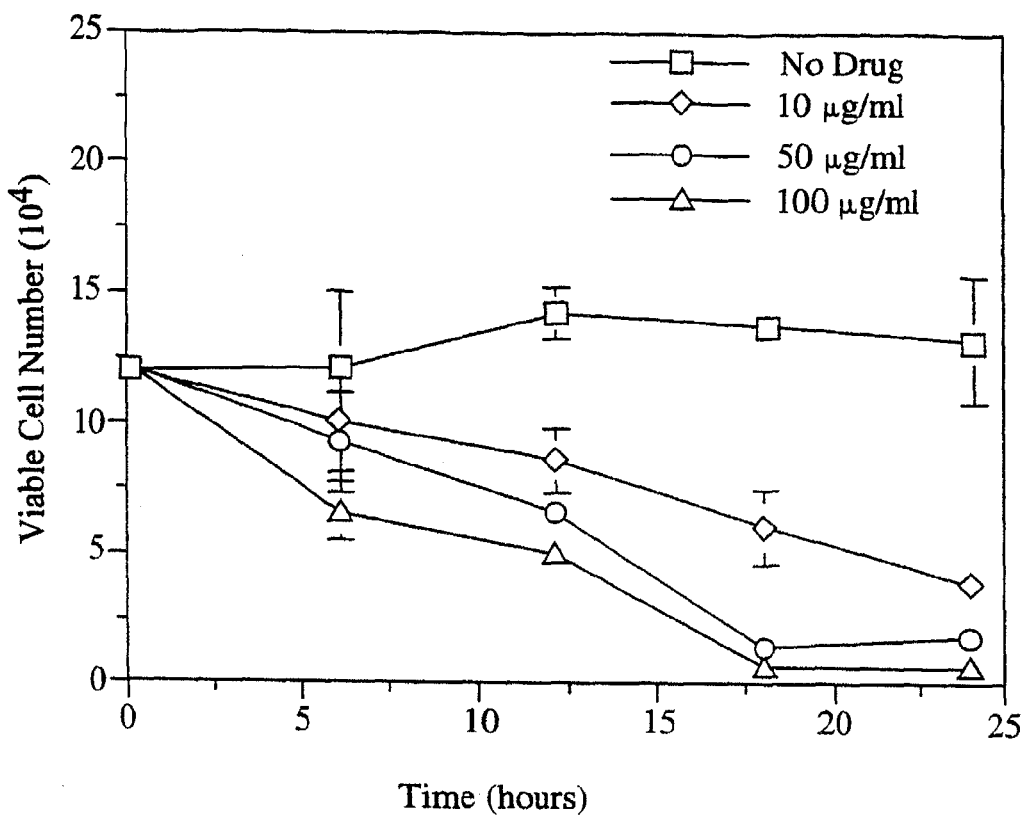
FIG. 3Ai
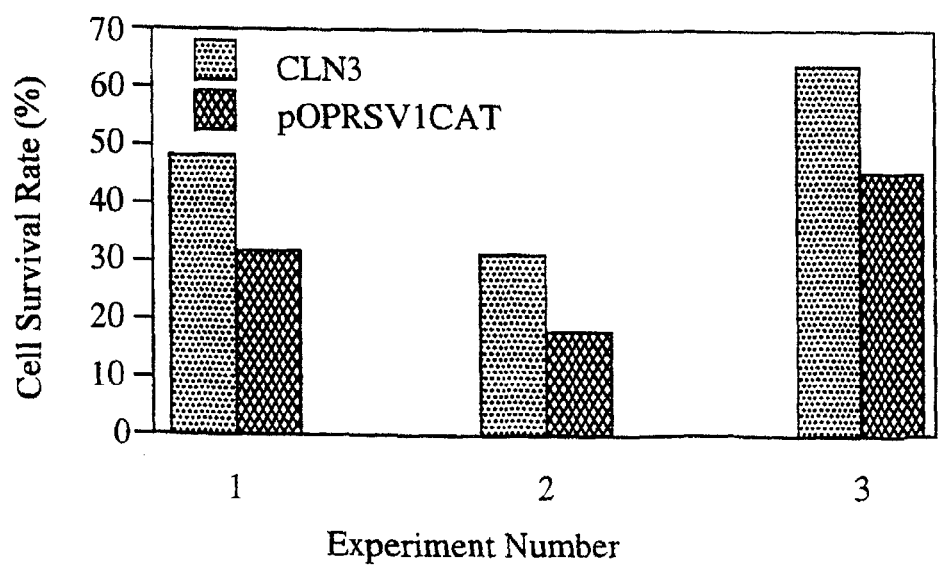
FIG. 3Aii

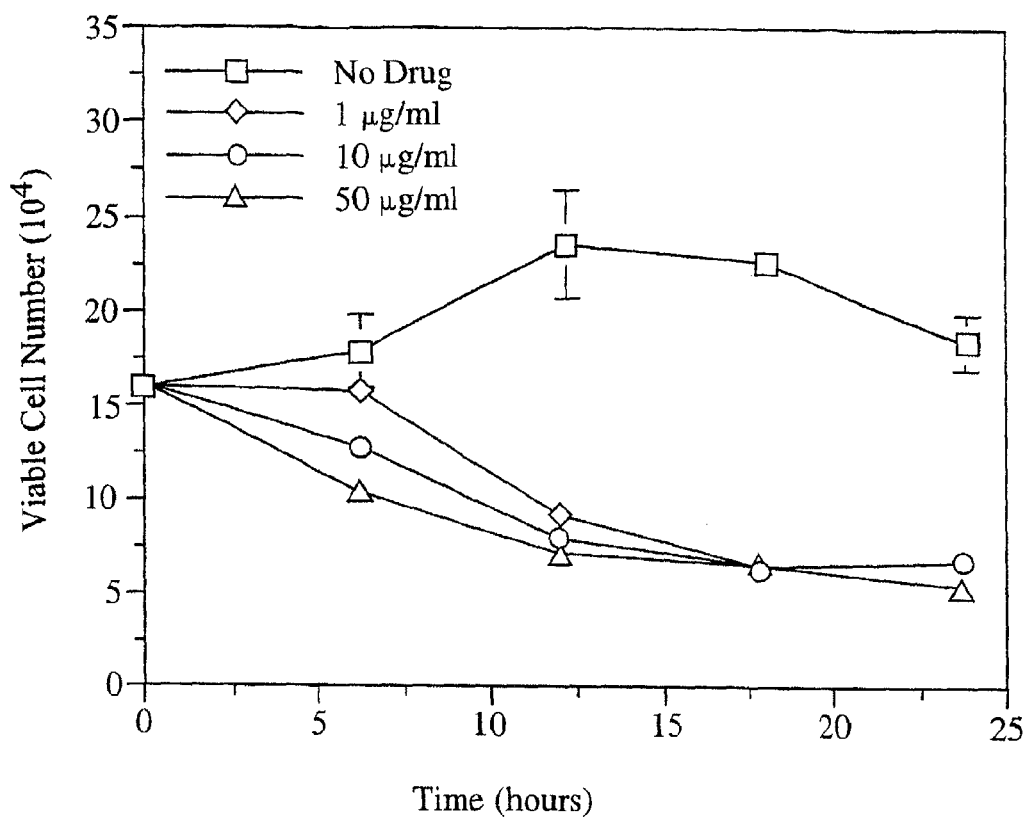
FIG. 3Bi
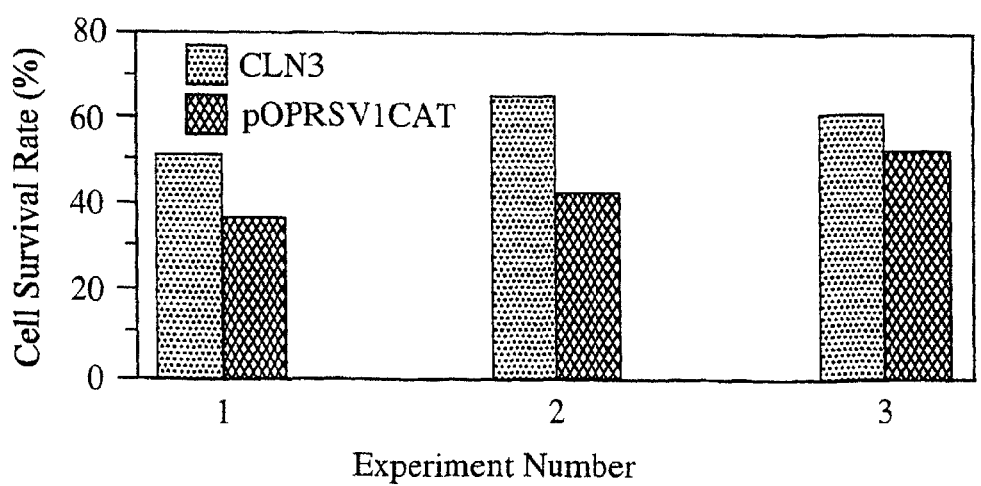
FIG. 3Bii

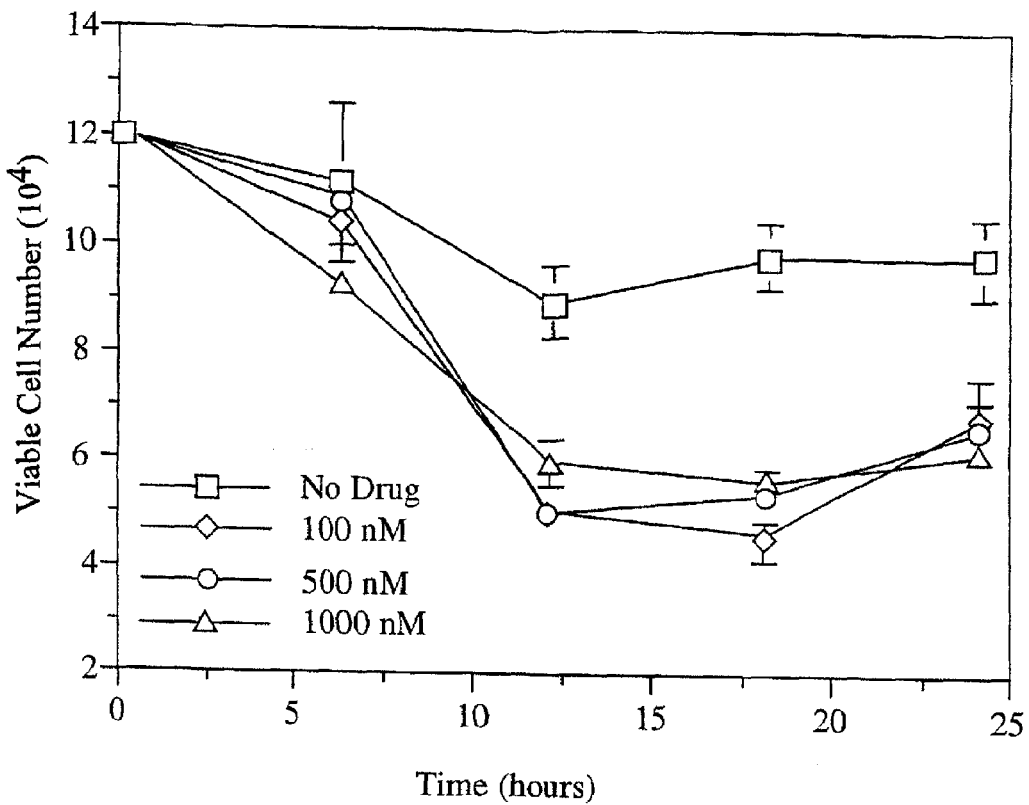
FIG. 3Ci
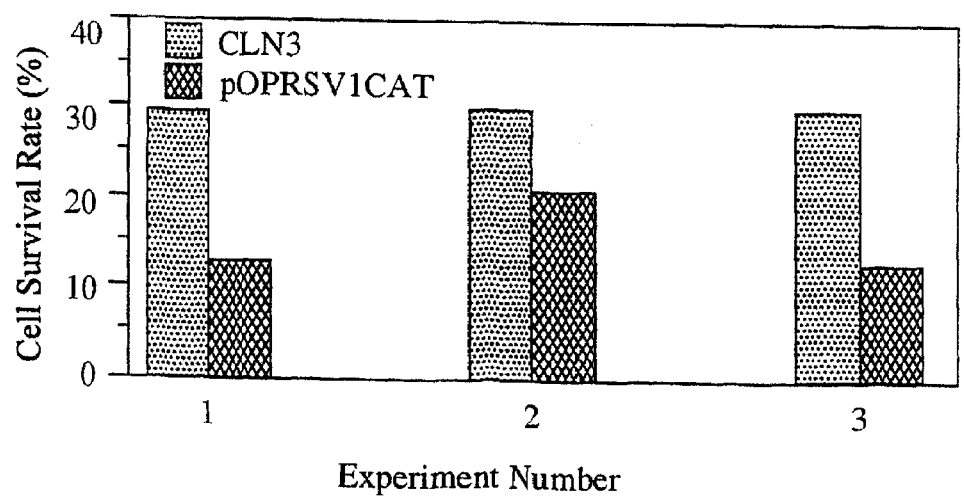
FIG. 3Cii

METHODS OF SCREENING FOR RISK OF PROLIFERATIVE DISEASE AND METHODS FOR THE TREATMENT OF PROLIFERATIVE DISEASE

This application is a National Stage filing under 35 USC 371 of PCT/US99/24695, filed Oct. 21, 1999, which claims priority to U.S. Provisional Application 60/105,262, filed Oct. 22, 1998.

The present invention was made with Government support under grant RO1-NS30170 from the National Institutes of Health. The Government has certain rights to this invention.

FIELD OF THE INVENTION

The present invention involves methods of screening for risk of proliferative diseases such as cancer. The screening may be a diagnostic or prognostic screening. Methods of screening compounds for the treatment of proliferative diseases and methods of treating proliferative disease are also disclosed.

BACKGROUND OF THE INVENTION

The juvenile form of Batten disease is an autosomal recessive neurodegenerative disease of childhood (Boustany R -M, et al., *Am. J. Med. Genet. Suppl.* 5: 47–58 (1988)). It is clinically characterized by onset at age 5–6 years with progressive blindness, generalized and myoclonic seizures, cognitive and motor decline and death in the mid to late twenties (Boustany R -M and Kolodny E H *Rev. Neurol. (Paris)* 145: 105–110 (1989); Boustany R -M *Am. J. Med. Genet.* 42: 533–535 (1992); Boustany R -M and Filipek P *J. Inher. Metab. Dis.* 16: 252–255 (1993)).

The CLN3 gene hypothesized to underly juvenile Batten disease encodes a 438 amino acid protein containing six putative hydrophobic transmembrane domains (The International Batten Disease Consortium *Cell* 82: 949–957 (1995); Janes R W et al., *FEBS Lett.* 399: 75–77 (1996)). It is expressed in a variety of human tissues including brain. The CLN3 protein is highly conserved across species including dog, mouse, *Caenorhabditis elegans* and *Saccharomyces cerevisiae*: (Altshul S F, et al., *J. Mol. Biol.* 215: 403–410 (1990); Mitchison H M, et al., *Genomics* 40: 346–350 (1997)).

It has been debated whether the function of the intact CLN3 gene is antiapoptotic, and that its integrity might be necessary for neuronal and photoreceptor survival. (See, e.g., Howard M K, et al., *J. Neurochem.* 60:1783–1791 (1993); Kulkarni G V and McCulloch C A *J. Cell Sci.* 107:1169–1179 (1994); Kulkarni G V and McCulloch C A *J. Cell Sci.* 107: 1169–1179 (1994) Kulkarni G V and McCulloch C A *J. Cell Sci.* 107: 1169–1179 (1994); Walker P R, et al., *Cancer Res.* 51: 1078–1085 (1991); Bertand R, et al., *Exp. Cell Res.* 211: 314–321 (1994); Stoll C, et al., *Cancer Res.* 36: 2710–2713 (1976)). An antiapoptotic function for intact CLN3 is not generally accepted.

SUMMARY OF THE INVENTION

As discussed in detail below, the present invention is based in part on the demonstration of antiapoptotic function for CLN3, on the surprising demonstration of upregulation of CLN3 in cancer cells, and on the finding that downregulation of CLN3 cancer cells inhibits the growth of cancer cells.

A first aspect of the present invention is a method of screening a subject for a proliferative disease risk factor. The method comprises detecting the presence or absence of upregulation of the CLN3 gene in the subject. The upregulation of the CLN3 gene in the subject indicates the subject is at increased risk of developing a proliferative disease.

A second aspect of the present invention is a method of screening a compound for efficacy in the treatment of a proliferative disease. The method comprises providing a group of subjects characterized by either (a) the presence of upregulation of the CLN3 gene in the group or (b) the absence of upregulation of the CLN3 gene in the group. The compound to be tested is then administered to the subjects, and the efficacy of the compound in the treatment of the proliferative disease is determined.

A third aspect of the present invention is an in vitro method of screening compounds for efficacy in treating a proliferative disease. The method comprises determining in vitro whether the compound inhibits the expression of the CLN3 gene. The inhibition of expression of the CLN3 gene indicates the compound is useful in treating the proliferative disease.

A fourth aspect of the present invention is a method of screening compounds for efficacy in treating a proliferative disease. The method comprises determining in vitro whether said compound specifically binds to the CLN3 gene product. The binding of the compound to the CLN3 gene product indicates that the compound is useful in treating the proliferative disease.

A fifth aspect of the present invention is a method of inhibiting the growth of proliferative cells. The method comprises administering to the cells a vector containing and expressing a heterologous nucleic acid, wherein the heterologous encodes a product such as an antisense oligonucleotide that inhibits the expression of the CLN3 gene in the cells.

A sixth aspect of the present invention is a recombinant vector useful for of inhibiting the growth of proliferative cells. The vector contains and expresses in susceptible cells a heterologous nucleic acid, wherein said heterologous nucleic acid encodes a product that inhibits the expression of the CLN3 gene in said cells.

The present invention is explained in greater detail in the drawings herein and the specification set forth below.

BRIEF DESCRIPTION OF THE DRAWINGS

FIG. 1. Overexpression of CLN3 enhances the rate of NT2 cell growth.

FIG. 2. CLN3 protects from serum starvation induced growth inhibition.

FIG. 3. CLN3 rescues NT2 cells from drug induced apoptosis.

FIG. 3A. CLN3 rescues from etoposide induced apoptosis: (i) For dose response curves, NT2 cells were treated with varying concentrations of etoposide and harvested at 6, 12, 18 and 24 h intervals. Viable cells were counted by the trypan blue method. Each data point is an average of three samples; (ii) NT2 cells that stably overexpress CLN3 were treated with etoposide (10 µg/ml) for 18 h and the viable cells were counted by the trypan blue method. The bargrams show the survival rate (ratio of viable cells in drug treated to untreated samples) of drug treated NT2 cells overexpressing CLN3 compared to treated cells transfected with vector alone. Results are shown from three separate experiments, each carried out in triplicate.

FIG. 3B. CLN3 rescues from vincristine induced apoptosis: (i) Dose response curve was determined by treating NT2 cells with varying concentrations of vincristine and counting the viable cells by the trypan blue method at various time intervals; (ii) NT2 cells stably transfected with CLN3 or vector alone were treated with vincristine (1 µg/ml for 18 h) and the survival rate determined by viability assay using trypan blue. The result shown is for three separate experiments, each performed in triplicate. The bargram compares the survival rate of CLN3-overexpressing and control cells following treatment with vincristine.

FIG. 3C. CLN3 rescues from staurosporine induced apoptosis: (i) Dose response curves for staurosporine in NT2 cells are shown. Viability was assessed at various time intervals by the trypan blue method; (ii) NT2 cells stably overexpressing CLN3 were treated with 500 nM staurosporine for 18 h. Survival rate was determined by the trypan blue method and is shown for three separate experiments, each carried out in triplicate. The bargram compares the survival rate of CLN3 overexpressing and control cells following staurosporine treatment, and the table shows protection and degree of protection afforded by CLN3 overexpression.

|  | Untreated pmoles/nmoles phospholipid | Vincristine treated pmoles/nmoles phospholipid | % Change in ceramide Treated-untreated/ untreated |
|---|---|---|---|
| Transient transfection |  |  |  |
| CLN3-pCMY4 | 4.62 ± 0.34 | 5.45 ± 0.50 | +18.0% |
| pCMV4 | 4.68 ± 0.4 | 5.92 ± 0.46 | +25.5% |
| Stable transfection |  |  |  |
| CLN3-Poprsv1CAT | 2.47 ± 0.13 | 2.03 ± 0.14 | −17.8% |
| pOPRSV1CAT | 13.6 ± 0.04 | 20 ± 0.1 | +47.0% |

Figure 5A:
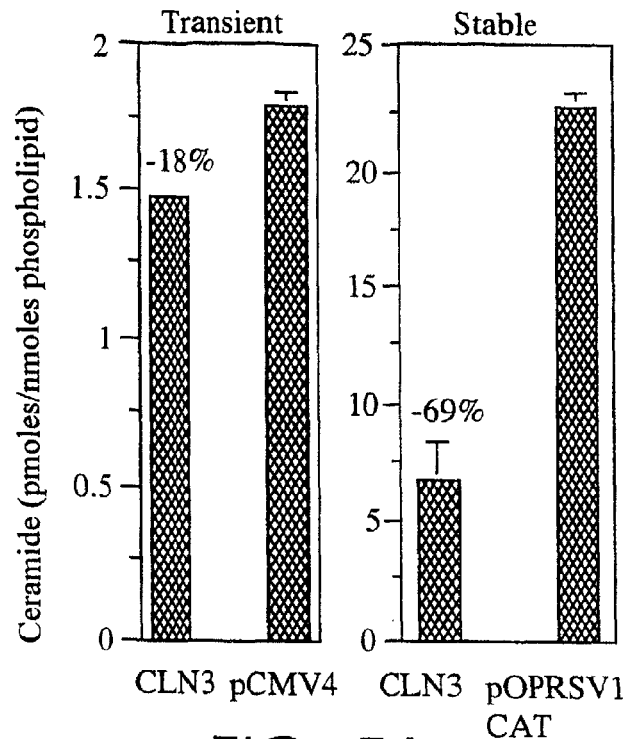
FIG. 5A. Overexpression of CLN3 lowers the level of endogenous ceramide in NT2 cells. NT2 cells were either transiently transfected with CLN3-CMV4 (left panel) or stably transfected with CLN3-OPRSV1CAT (right panel) and subjected to lipid extraction followed by measurement of ceramide. Each experiment was performed twice and in duplicate. The average percent drop in ceramide levels of NT2 cells overexpressing CLN3 compared to control cells is indicated within the bargraphs.
Figure 5B:
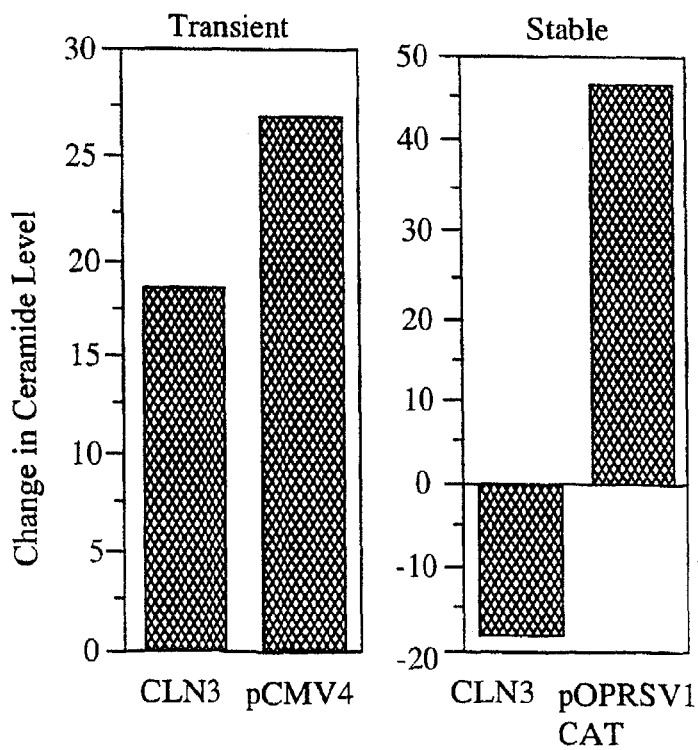
FIG. 5B. CLN3 overexpression prevents activation of ceramide by vincristine. NT2 cells transiently (left panel) or stably (right panel) overexpressing CLN3 and the appropriate controls were all treated with vincristine (1 µg/ml) prior to ceramide quantitation. Absolute ceramide values were expressed as pmoles/nmoles phospholipid and are shown below. The change in ceramide level for each cell line following vincristine treatment was calculated as the percent change in ceramide between vincristine treated and untreated cells and plotted. Results are an average of two experiments.
Figure 5C:
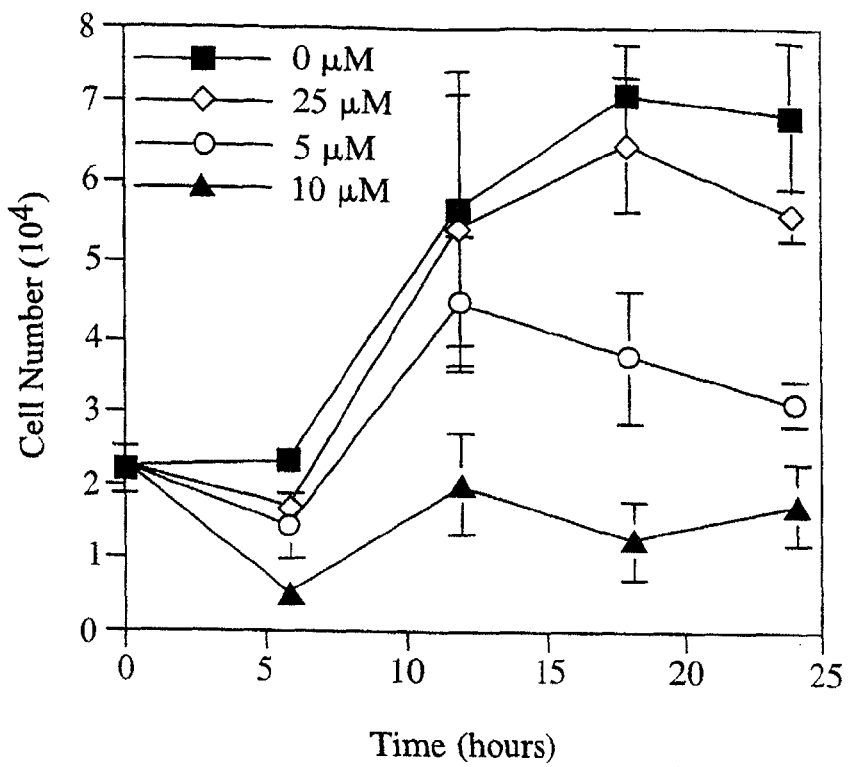
FIG. 5. CLN3 modulates ceramide formation.

FIG. 5C. Ceramide causes apoptosis in NT2 cells. Equal numbers of NT2 cells were plated and treated with increasing concentrations of $C_2$-ceramide. Cells were counted by the trypan blue method at 6, 12, 18 and 24 hour intervals. Each data point is an average of three samples.

Figure 5D:
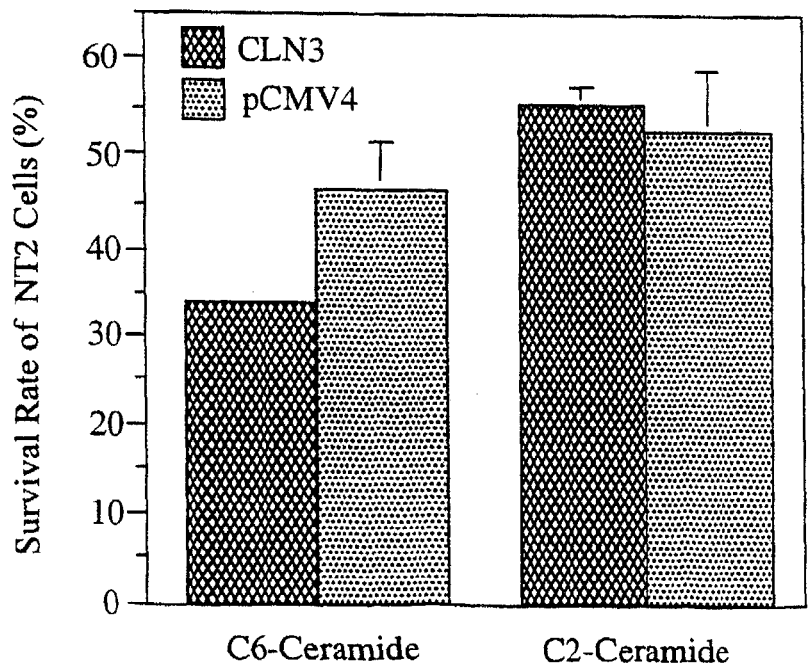

FIG. 5D. CLN3 does not protect NT2 cells from ceramide induced apoptosis. NT2 cells transiently transfected with CLN3 were treated with 5 μM of either $C_2$- or $C_6$-ceramide for 18 hours. Cells were then harvested and viability assessed by the trypan blue method. The data represents averages of three separate experiments (p>0.2).

Figure 6:
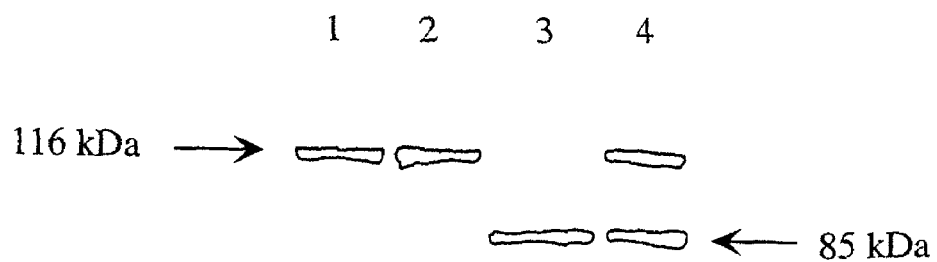

FIG. 6. CLN3 protects PARP from proteolysis in NT2 cells. NT2 cells were transiently transfected with CLN3 or pCMV4 and treated with etoposide (10 μg/ml) for 18 hours. Total protein was harvested from cells and analyzed for proteolysis of PARP from 116 kDa to the 85 kDa fragment by Western blotting using a polyclonal anti-PARP antibody. Lanes 1 and 3 are transfected with pCMV4, lanes 2 and 4 are transfected with CLN3-pCMV4, and lanes 3 and 4 are treated with etoposide.

Figure 7:
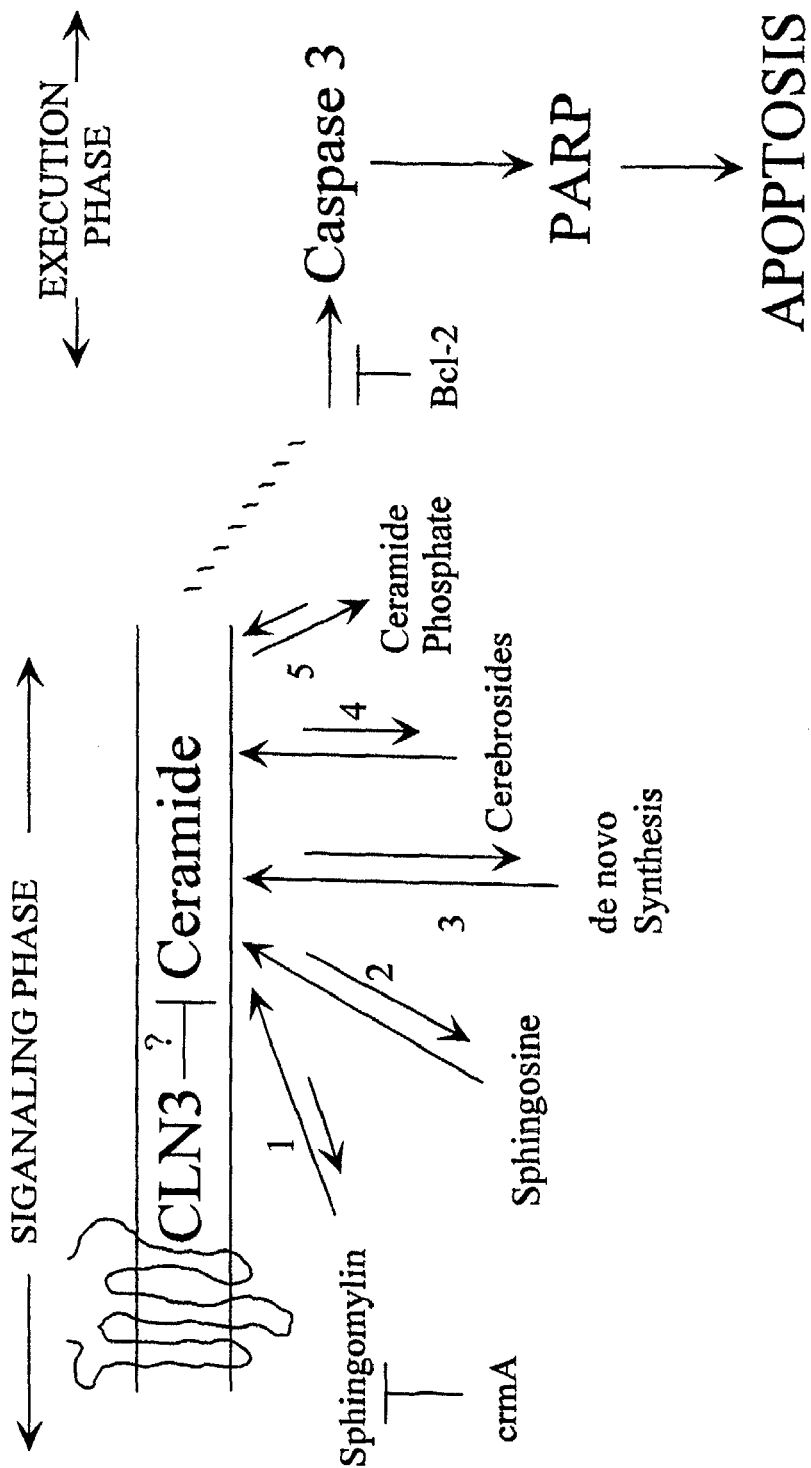

FIG. 7. Proposed role for CLN3 in positive regulation of cell growth. CLN3 acts upstream of ceramide and may regulate one of a number of enzymes implicated in ceramide metabolism such as: acid or neutral sphingomyelinase (1), ceramidase (2), ceramide synthase (3), cerebroside synthase (4), and ceramide kinase (5).

Figure 8:
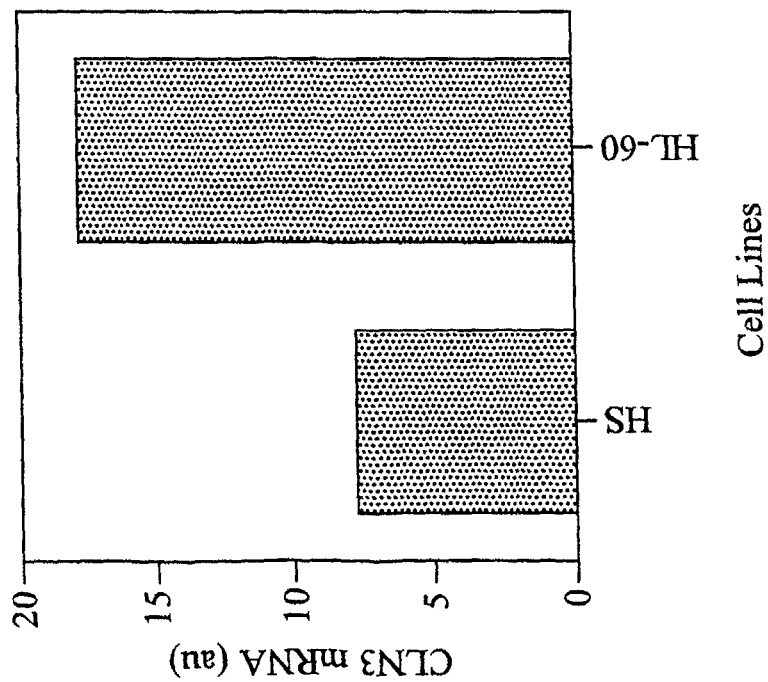

FIG. 8. Leukemia cell line HL-60 shows an overexpression of CLN3 compared to the transformed lymphoma cell line HS.

FIG. 8A. Column graph shows results of quantitative RT-PCR analysis expressed as arbitrary units of CLN3 overexpression. HL-60 cells had 2.3 times higher level of CLN3 mRNA compared to HS cells.

FIG. 8B. 10 μl each of HS and HL-60 cDNA, synthesized from the RT reaction, way hybridized with $\alpha^{32}$P-dCTP in the PCR reaction. The amplified DNAs were separated on 8% polyacrylamide gels and visualized by autoradiography. Autoradiogram shows the amplified 289 by fragment of CLN3 and 85 bp fragment of cyclophilin (the internal control) for each cell line. The amplified signal was quantitated on a Molecular Dynamics phosphorimager using ImageQuant software.

Figure 9:
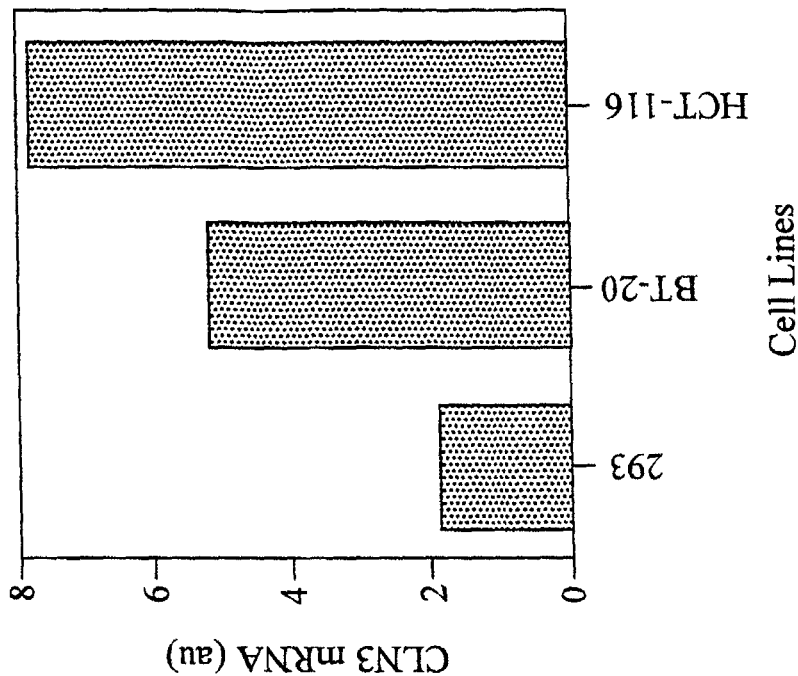

FIG. 9. Both the breast cancer cell line BT-20 and the colon cancer cell line HCT-116 shows an overexpression CLN3 compared to the control 293, a kidney epithelial cell line. Column graph shows results of quantitative RT-PCR analysis expressed as arbitrary units of CLN3 overexpression. CLN3 mRNS levels were 2.8 and 4.1 times more in BT-20 and HCT-116, respectively, than in the control.

Figure 10:
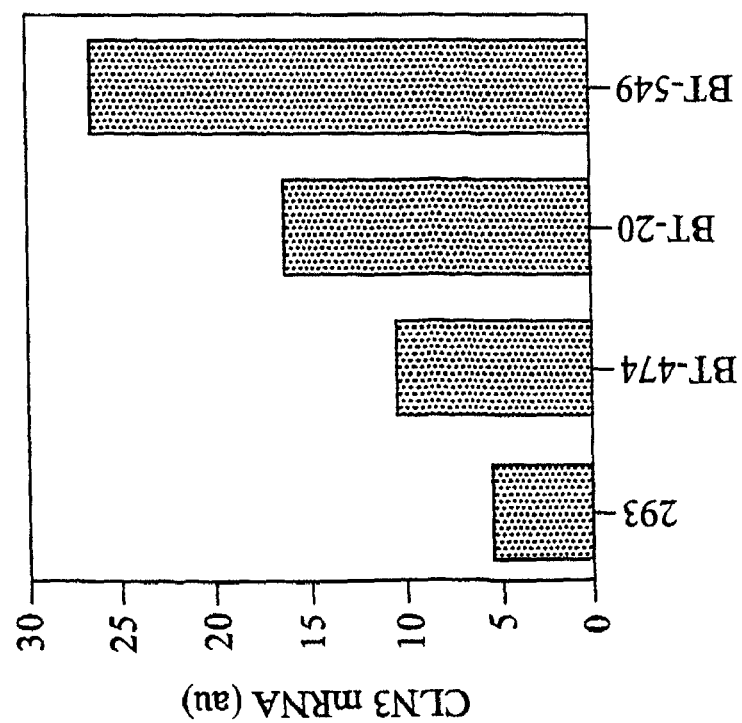

FIG. 10. The breast cancer cell lines BT-20, BT-474, and BT-549 all show an overexpression of CLN3 compared to the control 293, a kidney epithelial cell line. Column graph shows results of quantitative RT-PCR analysis expressed as arbitrary units of CLN3 overexpression. BT-474, BT-20, and BT-549 had 1.9, 3.0, and 4.8 times more CLN3 expression than the control, respectively.

Figure 11:
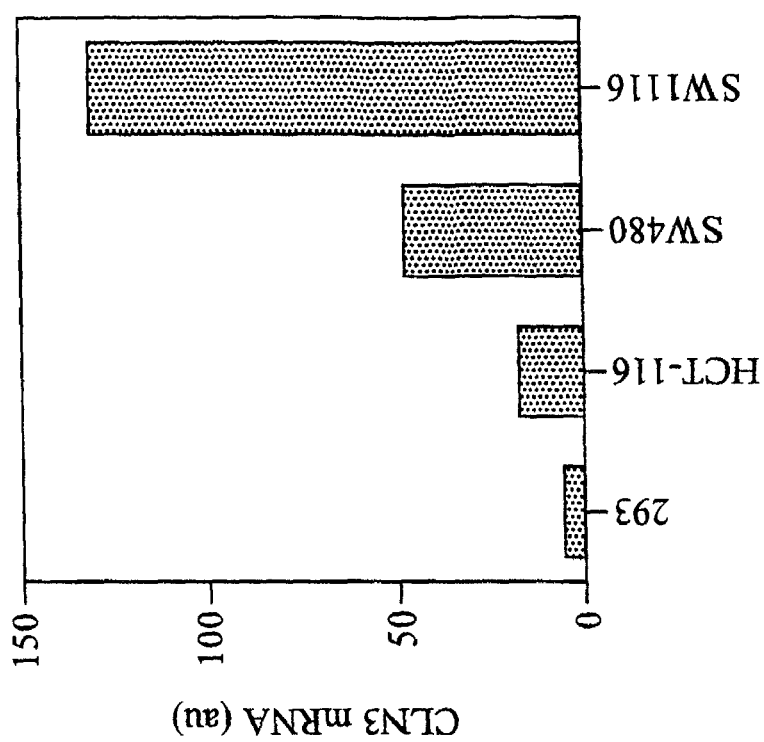

FIG. 11. The colon cancer cell lines HCT-116, SW480, and SW1116 all show an overexpression of CLN3 compared to the control 293, a kidney epithelial cell line. Column graph shows results of quantitative RT-PCR analysis expressed as arbitrary units of CLN3 overexpression. HCT-116 and SW480 had 3.0 and 7.7 times more CLN3 expression than the control, respectively. SW1116 had a dramatic 21.5 times the CLN3 mRNA level than did the control.

Figure 12:
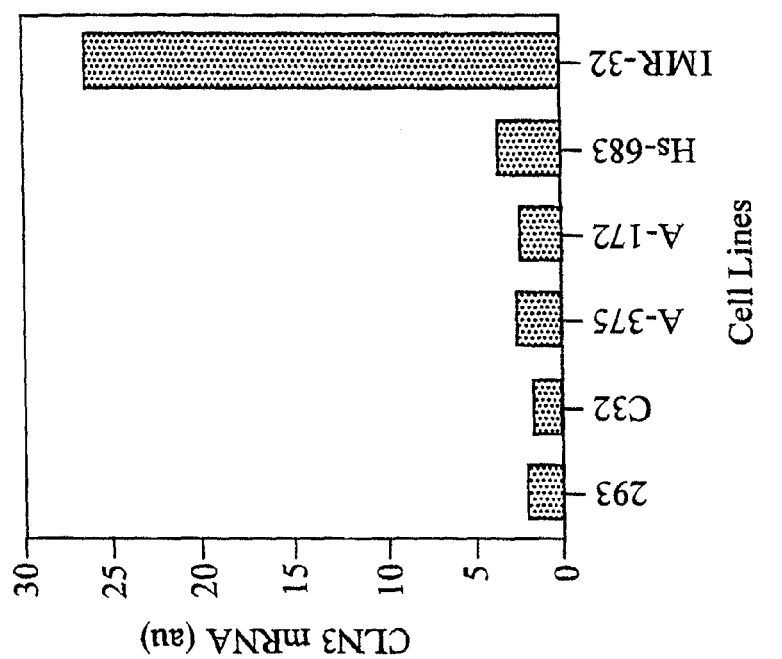

FIG. 12. Comparison of the CLN3 mRNA expression in two melanoma cell lines, C32 and A-375, neuroblastoma cell line IMR-32, glioma cell line Hs683, and glioblastoma cell line A-172 to the control 293, a kidney epithelial cell line. Column graph shows results of quantitative RT-PCR analysis expressed as arbitrary units of CLN3 overexpression. C32 actually had less CLN3 expressed, at 0.8 times, than did the control. Both A-375 and A-172 had a slight overexpression of CLN3, with 1.2 times more than the control. Hs683 had 1.7 times the CLN3 expression compared to the control. IMR-32 had a notable 12.7 times the CLN3 expression compared to the control.

Figure 13:
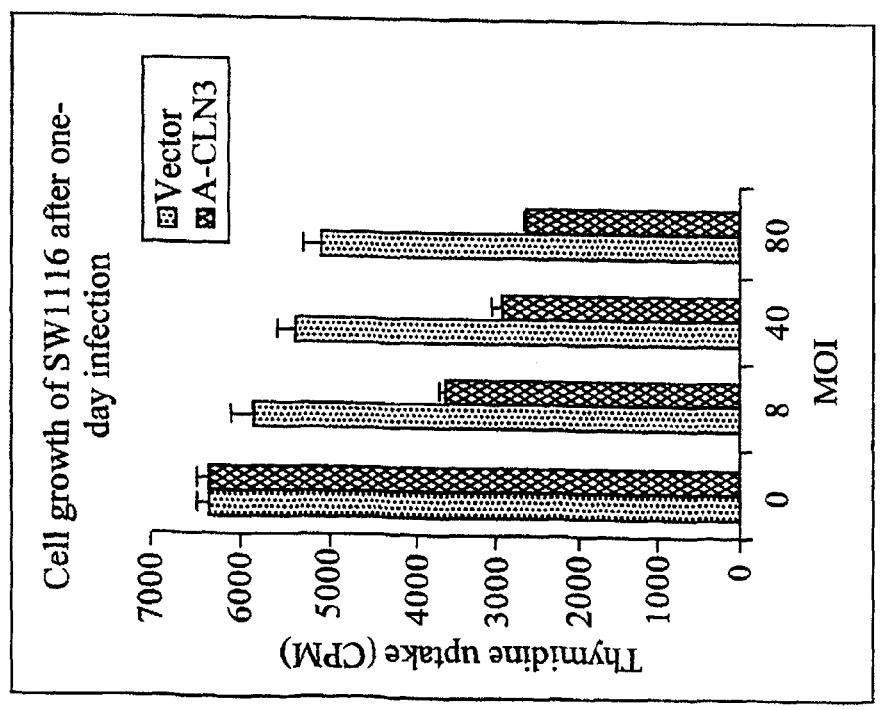

FIG. 13 shows the inhibition of growth of SW1116 colon cancer cells one day after infection with a CLN3 antisense vector.

Figure 14:
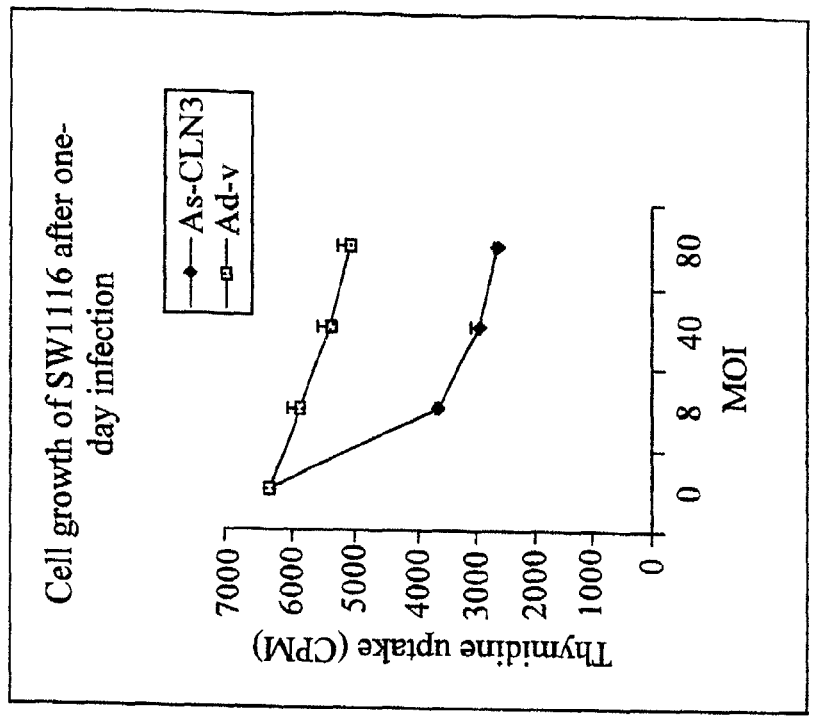

FIG. 14 shows the inhibition growth of SW1116 cells one day after infection with a CLN3 antisense vector.

Figure 15:
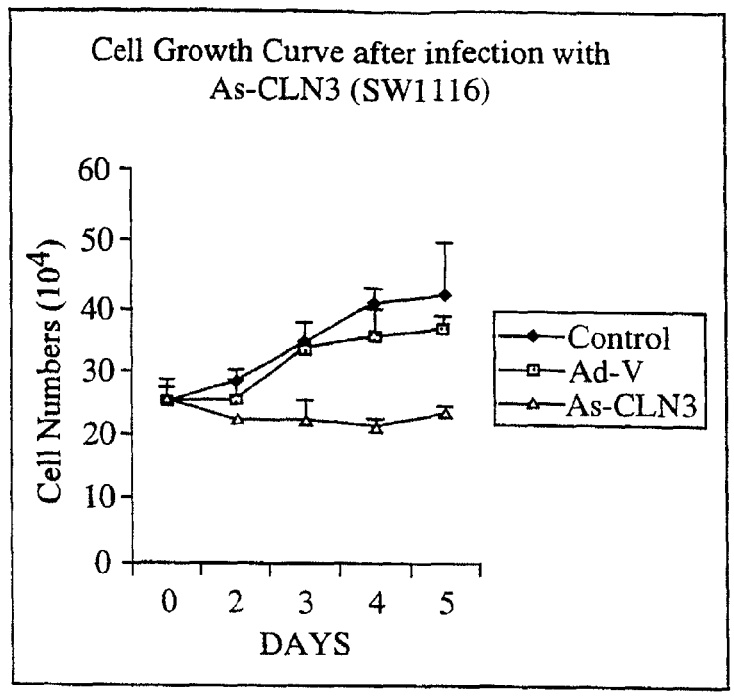

FIG. 15 shows the inhibition of growth of SW1116 at various times after infection with a CLN3 antisense vector.

Figure 16:
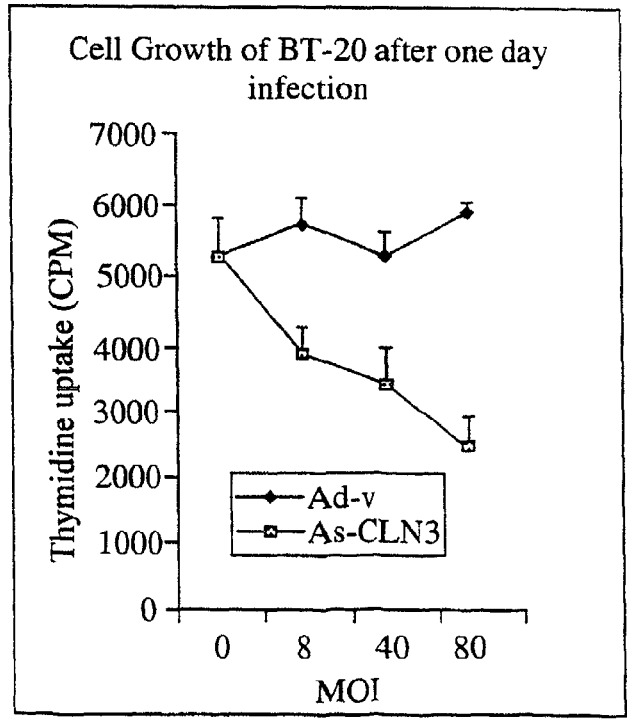

FIG. 16 shows the inhibition of growth of BT-20 breast cancer cells one day after infection with a CLN3 antisense vector.

Figure 17:
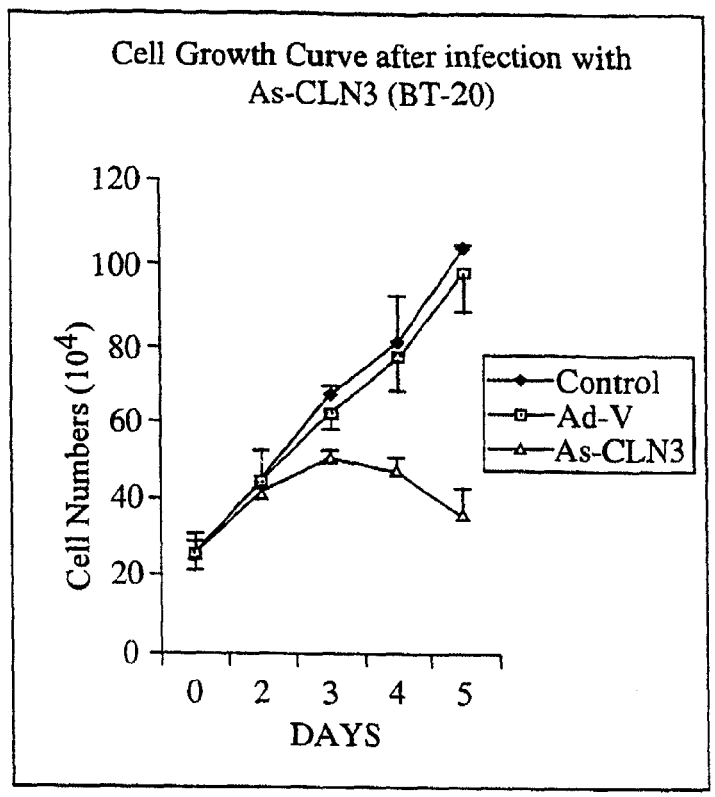

FIG. 17 shows the cell growth curve of BT-20 cells at various times after infection with a CLN3 antisense vector.

Figure 18:
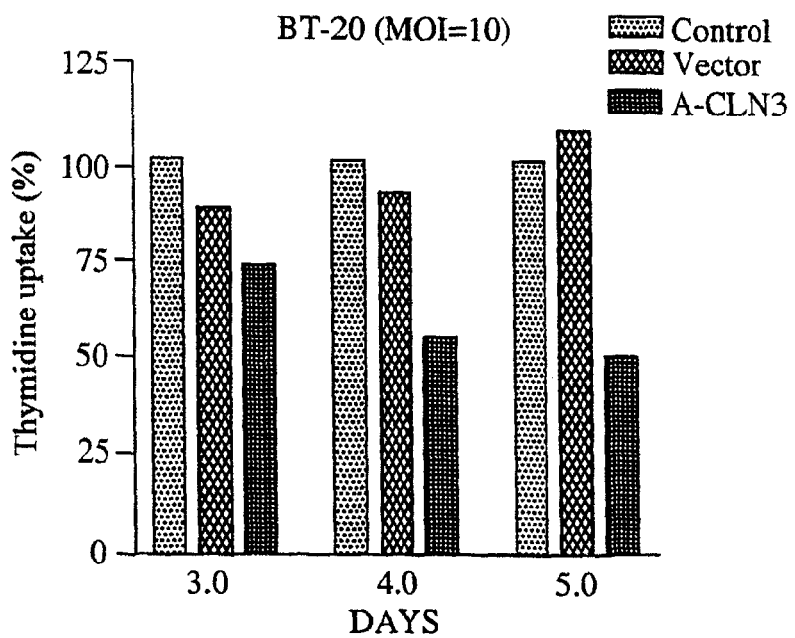

FIG. 18 shows the inhibition of growth of BT-20 cells at various times after infection with a CLN3 antisense vector.

DETAILED DESCRIPTION OF PREFERRED EMBODIMENTS

Amino acid sequences disclosed herein are presented in the amino to carboxy direction, from left to right. The amino and carboxy groups are not presented in the sequence. Nucleotide sequences are presented herein by single strand only, in the 5' to 3' direction.

The production of cloned genes, recombinant DNA, recombinant vectors, proteins and protein fragments by genetic engineering is well known, and can be carried out in accordance with known techniques. See, e.g., U.S. Pat. No. 5,585,269 to Earp et al.; U.S. Pat. No. 5,468,634 to Liu; and U.S. Pat. No. 5,629,407 to Xiong et al. (the disclosures of all United States patent references cited herein are to be incorporated herein by reference in their entirety.

The CLN3 gene referred to herein is known, and is also referred to as the Batten Disease gene. See, e.g., The International Batten Disease Consortium, Isolation of a Novel Gene Underlying Batten Disease, CLN3, Cell, 82, 949–957 (1995). The gene may be of any species depending upon the subject and/or the particular use thereof, but is typically mammalian and preferably human.

The term "risk factor" as used herein indicates subjects that possess the indicated trait or factor face an increased risk of developing the corresponding gene than subjects who do not possess the risk factor.

The term "upregulation" as used herein with respect to the CLN3 gene means greater levels of the gene product are produced as compared to corresponding normal subjects.

The term "treat" as used herein refers to any type of treatment that imparts a clinical improvement in the condition of the patient, or delays the progression of the disease.

The term "proliferative disease" as used herein refers to both cancer and non-cancer disease. Preferably the proliferative disease is one characterized by increased expression of the CLN3 gene product in afflicted patients. Illustrative non-cancer diseases include inflammatory and/or immunoproliferative disorders such as arthritis, fibrosis, asthma and allergies. The invention can be used to screen for risk of and/or treat a variety of different types of cancer cells, particularly malignant (and preferably solid) tumors of epithelial or mesenchymal cells. Examples of cancers that can be screened for risk of and/or treated by the present invention include breast cancer, melanoma, lung cancer, colon cancer, leukemia (a liquid or non-solid tumor), soft tissue and bone sarcomas, neuroendocrine tumors such as islet cell carcinoma or medullary carcinoma of the thyroid, squamous carcinomas (particularly of the head and neck), adenocarcinomas, etc. The treatment of breast cancer is a particularly preferred target for carrying out the present invention.

While the present invention is primarily concerned with the screening and treatment of human subjects, the invention may also be carried out on animal subjects such as dogs, cats, and horses for veterinary purposes.

1. Screening Applications.

As noted above, the present invention provides a method of screening a subject for a proliferative disease risk factor. The method comprises detecting the presence or absence of upregulation of the CLN3 gene in the subject. The upregulation of the CLN3 gene in the subject indicates the subject is at increased risk of developing a proliferative disease. Thus, the presence of the risk factor is determined from the upregulation of the CLN3 gene in the subject.

The method can be carried out whether or not the subject has been previously diagnosed as being afflicted with a proliferative disease, and whether or not the subject has been previously prognosed to be at risk of developing the proliferative disease.

The step of detecting whether the CLN3 gene is upregulated (that is, the gene product thereof is found at increased levels as compared to normal subjects), can be carried out by any suitable means. For example, the step may be carried out by detecting increased mRNA levels for the CLN3 gene in cells of the subject, or by detecting increased levels of the protein product of the CLN3 gene in cells of the subject.

When the subject has previously been diagnosed as afflicted with a proliferative disease, the method may be carried out to monitor the progression of that disease, or monitor the efficacy of drug treatments that the patient has undergone for the treatment of that disease. Decreased levels of expression of the CLN3 gene would be indicative of efficacy of the drug treatment.

As also noted above, the present invention also provides a method of screening a compound for efficacy in the treatment of a proliferative disease. The method comprises providing a group of subjects characterized by either (a) the presence of upregulation of the CLN3 gene in the group or (b) the absence of upregulation of the CLN3 gene in the group. The compound to be tested is then administered to the subjects, and the efficacy of the compound in the treatment of the proliferative disease is determined. It will be appreciated that not every member of the group need possess the desired trait, as long as a sufficient number in the group possess the desired trait so that the typical effect of the presence or absence of the trait in the group can be discerned. By incorporating this information into a drug trial, whether the upregulation of the CLN3 is present or absent in the group (or the group is divided into subgroups of those in whom upregulation is present and those in whom upregulation is absent) more accurate information can be obtained on the treatment of particular patients. It will be appreciated that it can be equally valuable to determine that a particular drug is efficacious for a particular patient population as it is to determin that a particular drug is not efficacious for a particular patient population, as the latter information can at least be useful in directing therapy to more promising treatments.

In vitro methods of screening compounds for efficacy in treating a proliferative disease are also disclosed herein. In general, in one embodiment, such methods comprise determining in vitro whether the compound inhibits the expression of the CLN3 gene (preferably the mammalian gene, and most preferably the human gene). The inhibition of expression of the CLN3 gene indicates the compound is useful in treating the proliferative disease. Numerous such methods are available. The methods can be carried out in a cell or cells, or can be carried out in essentially cell free preparation. The method can be carried out by screening for compounds that specifically disrupt either transcription or translation of the CLN3 gene. The compound to be screened may be a member of a library of compounds (the term "compound" as used in this respect referring to both small organic compounds and other therapeutic agents such as recombinant viral vectors). The method may be carried out as a single assay, or may be implemented in the form of a high throughput screen in accordance with a variety of known techniques.

In another embodiment, the method of screening compounds for efficacy in treating a proliferative disease comprises determining in vitro whether said compound specifically binds to the CLN3 gene product (preferably the mammalian gene product; most preferably the human gene product). The determining step can be carried out by screening for binding of a test compound or probe molecule to the entire full length CLN3 gene product, or to a peptide fragment thereof (e.g., a fragment of from 5, 10 or 20 amino acids in length up to the full length of the CLN3 gene product. The binding of the compound to the CLN3 gene product indicates that the compound is useful in treating the proliferative disease. Such techniques can be carried out by contacting a probe compound to the CLN3 gene product or fragment thereof in any of the variety of known combinatorial chemistry techniques (including but not limited to split pool techniques, chip-based techniques and pin-based techniques). Any suitable solid support can be used to imobilize the CLN3 gene product or a fragment thereof to find specific binding partners thereto (or immobilize the members of the library against which the CLN3 gene product or fragment thereof is contacted to find specific binding partners thereto), and numerous different solid supports are well known to those skilled in the art. Examples of suitable materials from which the solid support may be formed include cellulose, poreglass, silica gel, polystyrene, particularly polystyrene cross-linked with divinylbenzene, grafted copolymers such as polyethyleneglycol/polystyrene, polyacrylamide, latex, dimethylacrylamide, particularly cross-linked with N,N'bis-acrylolyl ethylene diamine and comprising N-t-butoxycarbonyl-beta-alanyl-N'acrylolyl hexamethylene diamine, composites such as glass coated with a hydrophobic polymer such as cross-linked polystyrene or a fluorinated ethylene polymer to which is grafted linear polystyrene, and the like. Thus the term "solid support" includes materials conventionally considered to be semi-solid supports. General reviews of useful solid supports that include a covalently-linked reactive functionality may be found in Atherton et al., *Prospectives in Peptide Chemistry*, Karger, 101–117 (1981); Amamath et al., *Chem. Rev.* 77: 183 (1977); and Fridkin, The Peptides, Vol. 2, Chapter 3, Academic Press, Inc., pp 333–363 (1979). The solid support may take any suitable form, such as a bead or microparticle, a tube, a plate, a microtiter plate well, a glass microscope cover slip, etc.

The present invention can be used with probe molecules, or libraries (where groups of different probe molecules are employed), of any type. In general, such probe molecules are organic compounds, including but not limited to that may be used to carry out the present include oligomers, non-oligomers, or combinations thereof. Non-oligomers include a wide variety of organic molecules, such as heterocyclics, aromatics, alicyclics, aliphatics and combinations thereof, comprising steroids, antibiotics, enzyme inhibitors, ligands, hormones, drugs, alkaloids, opioids, benzodiazepenes, terpenes, prophyrins, toxins, catalysts, as well as combinations thereof. Oligomers include peptides (that is, oligopeptides) and proteins, oligonucleotides (the term oligonucleotide also referred to simply as "nucleotide, herein) such as DNA and RNA, oligosaccharides, polylipids, polyesters, polyamides, polyurethanes, polyureas, polyethers, poly (phosphorus derivatives) such as phosphates, phosphonates, phosphoramides, phosphonamides, phosphites, phosphinamides, etc., poly (sulfur derivatives) such as sulfones, sulfonates, sulfites, sulfonamides, sulfenamides, etc., where for the phosphorous and sulfur derivatives the indicated heteroatom for the most part will be bonded to C, H, N, O or S, and combinations thereof. Numerous methods of synthesizing or applying such probe molecules on solid supports (where the probe molecule may be either covalently or non-covalently bound to the solid support) are known, and such probe molecules can be made in accordance with procedures known to those skilled in the art. See, e.g., U.S. Pat. No. 5,565,324 to Still et al., U.S. Pat. No. 5,284,514 to Ellman et al., U.S. Pat. No. 5,445,934 to Fodor et al. (the disclosures of all United States patents cited herein are to be incorporated herein by reference in their entirety).

Test compounds used to carry out the present invention may be of any type, including both oligomers or non-oligomers of the types described above in connection with probe molecules above. Again, such test compounds are known and can be prepared in accordance with known techniques.

Where multiple different probe molecules are desired to be tested, a screening substrate useful for the high throughput screening of molecular interactions, such as in "chip-based" and "pin-based" combinatorial chemistry techniques, can be prepared in accordance with known techniques. All can be prepared in accordance with known techniques. See, e.g., U.S. Pat. No. 5,445,934 to Fodor et al., U.S. Pat. No. 5,288,514 to Ellman, and U.S. Pat. No. 5,624,711 to Sundberg et al.

In the alternative, screening of libraries of probe molecules may be carried out with mixtures of solid supports as used in "split-pool" combinatorial chemistry techniques. Such mixtures can be prepared in accordance with procedures known in the art, and tag components can be added to the discreet solid supports in accordance with procedures known in the art. See, e.g., U.S. Pat. No. 5,565,324 to Still et al.

2. Vectors and Administration.

Vectors used to carry out the present invention are, in general, RNA virus or DNA virus vectors, such as lentivirus vectors, papovavirus vectors (e.g., SV40 vectors and polyoma vectors), adenovirus vectors and adeno-associated virus vectors. See generally T. Friedmann, Science 244, 1275 16 (June 1989).

Examples of lentivirus vectors that may be used to carry out the present invention include Moloney Murine Leukemia Virus vectors, such as those described in U.S. Pat. No. 5,707,865 to Kohn.

Any adenovirus vector can be used to carry out the present invention. See, e.g., U.S. Pat. No. 5,518,913, U.S. Pat. No. 5,670,488, U.S. Pat. No. 5,589,377; U.S. Pat. No. 5,616,326; U.S. Pat. No. 5,436,146; and U.S. Pat. No. 5,585,362. The adenovirus can be modified to alter or broaden the natural tropism thereof, as described in S. Woo, *Adenovirus redirected*, Nature Biotechnology 14, 1538 (November 1996).

Any adeno-associated virus vector (or AAV vector) can also be used to carry out the present invention. See, e.g., U.S. Pat. No. 5,681,731; U.S. Pat. No. 5,677,158; U.S. Pat. No. 5,658,776; U.S. Pat. No. 5,658,776; U.S. Pat. No. 5,622,856; U.S. Pat. No. 5,604,090; U.S. Pat. No. 5,589,377; U.S. Pat. No. 5,587,308; U.S. Pat. No. 5,474,935; U.S. Pat. No. 5,436,146; U.S. Pat. No. 5,354,678; U.S. Pat. No. 5,252,479; U.S. Pat. No. 5,173,414; U.S. Pat. No. 5,139,941; and U.S. Pat. No. 4,797,368.

The regulatory sequences, or the transcriptional and translational control sequences, in the vectors can be of any suitable source, so long as they effect expression of the heterologous nucleic acid in the target cells. For example, commonly used promoters are the LacZ promoter, and promoters derived from polyoma, Adenovirus 2, and Simian virus 40 (SV40). See, e.g., U.S. Pat. No. 4,599,308.

The heterologous nucleic acid may encode any product that inhibits the expression of the CLN3 gene in cells infected by the vector, such as an antisense oligonucleotide that specifically binds to the CLN3 mRNA to disrupt or inhibit translation thereof, a ribozyme that specifically binds to the CLN3 mRNA to disrupt or inhibit translation thereof, or a triplex nucleic acid that specifically binds to the CLN3 duplex DNA and disrupts or inhibits transcription thereof. All of these may be carried out in accordance with known techniques, as (for example) described in U.S. Pat. Nos. 5,650,316; 5,176,996, or 5,650,316 for triplex compounds, in U.S. Pat. Nos. 5,811,537; 5,801,154; and 5,734,039 for antisense compounds, and in U.S. Pat. Nos. 5,817,635; 5,811,300; 5,773,260; 5,766,942; 5,747,335; and 5,646,020 for ribozymes (the disclosures of which are incorporated by reference herein in their entirety). The length of the heterologous nucleic acid is not critical so long as the intended function is achieved, but the heterologous nucleic acid is typically from 5, 8, 10 or 20 nucleic acids in length up to 100, 200, 500 or 1000 nucleic acids in length, up to a length equal the full length of the CLN3 gene.

Once prepared, the recombinant vector can be reproduced by (a) propagating the vector in a cell culture, the cell culture comprising cells that permit the growth and reproduction of the vector therein; and then (b) collecting the recombinant vector from the cell culture, all in accordance with known techniques. The viral vectors collected from the culture may be separated from the culture medium in accordance with known techniques, and combined with a suitable pharmaceutical carrier for administration to a subject. Such pharmaceutical carriers include, but are not limited to, sterile pyrogen-free water or sterile pyrogen-free saline solution. If desired, the vectors may be packaged in liposomes for administration, in accordance with known techniques.

Any suitable route of administration can be used to carry out the present invention, depending upon the particular condition being treated. Suitable routes include, but are not limited to, intraveneous, intrarterial, intrathecal, intraperitoneal, intramuscular, and intralesional injection. Intralesional injection is currently preferred.

The dosage of the recombinant vector administered will depend upon factors such as the particular disorder, the particular vector chosen, the formulation of the vector, the condition of the patient, the route of administration, etc., and can be optimized for specific situations. In general, the dosage is from about $10^7$, $10^8$, or $10^9$ to about $10^{11}$, $10^{12}$, or $10^{13}$ plaque forming units (pfu).

In addition to their pharmaceutical or veterinary use, the recombinant vectors of the present invention (sometimes also referred to as "active agents" herein) are useful in vitro to distinguish cells in culture based on their response to the active agents, to induce apoptosis, etc. Such techniques are useful for both carrying out cell culture procedures and for drug screening purposes.

The present invention is described in further detail in the following non-limiting Examples. Abbreviations used herein are as follows: JNCL, juvenile neuronal ceroid lipofuscinosis; NT2, Ntera2/D1; NGF, nerve growth factor; ICE, interleukin-1 converting enzyme; PARP, poly (ADP-ribose) polymerase; RT-PCR, reverse transcription-polymerase chain reaction; PBS, phosphate buffered saline; DAB, 3,3'-diaminobenzidine; TUNEL, Tdt mediated dUTP nick end labeling. Drs. Terry Lerner and Jim Gusella graciously provided the CLN3 cDNA.

Example 1

CLN3 Defines a Novel Antiapoptotic Pathway Operative in Neurodegeneration and Mediated by Ceramide This example establishes a direct link between apoptosis and neurodegeneration in Batten disease at a molecular level.

I. Experimental Procedures

Transfections: NT2 cells (ATCC# CRL1973) were plated on 60 nm dishes at a density of $0.5 \times 10^6$ and grown at 37° C. in a 5% $CO_2$ atmosphere in DMEM supplemented with 10% fetal bovine serum and 100 units each of penicillin and streptomycin. The CLN3 cDNA was subcloned in the pCMV4 vector for transient transfections and in the pOPRSV1CAT vector or the pCEP4 vector (Invitrogen, Carlsbad, Calif.) for stable transfections (Andersson S, et al., *J. Biol. Chem.* 264: 8222–8229 (1989); Fieck A, et al., *Nucleic Acid Res.* 20: 1785–1791 (1992)). Transfections with the CLN3-pCMV4 construct or the CLN3-pOPRSV1CAT construct were carried out by the calcium phosphate method according to the manufacturer's protocol using the MBS transfection kit (Stratagene, LaJolla, Calif.). Transfections with the CLN3-pCEP4 construct were carried out using Superfect reagent (Qiagen, Valencia, Calif.) according to the manufacturer's method. Transiently transfected cells were harvested for all analyses within 48 hours of transfection. Stable clones were selected either with 500 µg/ml geneticin (CLN3-pOPRSV1CAT) or with 100 µg/ml hygromycin (CLN3-pCEP4) and subsequently grown under selective pressure.

Drug treatments: Dose response curves were established for etoposide, vincristine and staurosporine in NT2 cells (FIGS. 3Ai, 3Bi and 3Ci). Stably transfected NT2 cells and vector control cells were seeded at a density of $5 \times 10^4$ cells/well in 12-well plates, allowed to attach and then were treated with etoposide (10 µg/ml) or vincristine (1 µg/ml) or staurosporine (500 nM) for 18 h and the number of viable cells counted by the trypan blue assay. Survival represents the number of drug treated viable cells divided by the number of untreated viable cells and expressed as a percentage. Protection is calculated as the difference in survival between CLN3-overexpressing cells and the vector-transfected control cells. The degree of protection is calculated as the difference in survival between treated CLN3-overexpressing and vector control cells divided by the survival of treated vector control cells. The values are from three separate experiments, each of which was carried out in triplicate (FIGS. 3Aii, 3Bii, and 3Cii).

RT-PCR: Messenger RNA was isolated from NT2 cells by the oligo-dT-cellulose method using the QuickPrep Micro mRNA Purification kit (Pharmacia Fine Chemicals, Piscataway, N.J.). The mRNA was converted to cDNA by the reverse transcription (RT) reaction (Estus et al, 94). PCR reactions were set up with the first strand cDNA, 1 U of Taq polymerase and 5 µCi of $\alpha^{32}$P-dCTP in each reaction. The reactions were performed in Taq buffer containing 1.5 mM $MgCl_2$, 2.5 mM dCTP and 5 mM each of dATP, dGTP and dTTP. The primers used for amplification of CLN3 were 5' primer: 5'-GGTGGACAGTATTCAAGGG-3' (958–976, SEQ ID NO: 1) and 3' primer: 5'-CTTGGCAGAAAGAC-GAAC-3' (1229–1246, SEQ ID NO: 2). Cyclophilin was used as the internal control and primers used for cyclophilin amplification were the 5' primer: 5'-AAATGCTGGAC-CCAACAC-3' (317–334, SEQ ID NO: 3) and 3' primer: 5'-AAACACCACATGCTTGCC-3' (384–401, SEQ ID NO: 4). The reaction conditions used were 1 minute at 94° C., 1 minute at 50° C. and 2 minutes at 72° C. for 20 cycles. The PCR amplified products were analyzed on an 8% non-denaturing polyacrylamide gel that was dried and visualized by autoradiography. The amplified signal was quantitated using a PhosphorImager (Molecular Dynamics Inc., Sunnyvale, Calif.). The results are expressed as the ratio of CLN3 signal to that of the internal control cyclophilin. This provides a reproducible and comparative, semi-quantitative measure of CLN3 expression.

Western Blotting for CLN3 and PARP detection: The CLN3 antibody used in this study is a polyclonal antibody raised against the peptide sequence AAHDILSHKRTSGN-QSHVDP (SEQ ID NO: 5) corresponding to amino acids 58–77 of the CLN3 protein (Research Genetics, Huntsville, Ala.). Total cellular extracts for CLN3 detection were prepared from NT2 cells transfected with CLN3 or the appropriate vector control. Cells were washed with cold PBS and lysed in buffer (250 mM NaCl, 0.1% NP40, 50 mM Hepes, pH 7.0, 5 mM EDTA, 1 mM DTT, 1 mM PMSF) on ice for 10 min. The lysate was collected and clarified by centrifugation at 12,000×g for 10 min at 4° C. The supernatant was quantitated for total protein by the BioRad protein assay method. Equal amounts of total protein from each sample were electrophoresed on a 9% SDS-polyacrylamide gel in buffer containing 0.092 M glycine, 0.125 M Tris-OH and 2% SDS. The gel was transferred onto nitrocellulose membrane by semidry electroblotting and blocked by incubation in solution containing 3% BSA in TBST (10 mM Tris-HCl, pH 8.0, 150 mM NaCl, 0.05% Tween-20) buffer for one hour at 25° C. followed by incubation with the CLN3 antibody (IgG fraction) diluted in TBST, for 15 hours at 25° C. After extensive washes with TBST buffer, the membrane was incubated in a 1:5000 dilution of goat-anti-rabbit IgG conjugated with horseradish peroxidase for 30 minutes at 25° C. The blot was washed and developed using the chemiluminescence detection system (Amersham, Arlington Heights, Ill.).

For the PARP analysis, transfected NT2 cells were harvested by scraping in PBS followed by lysis in gel loading buffer containing 62.5 mM Tris-HCl pH 6.8, 6 M urea, 10% glycerol, 2% SDS, 0.003% bromophenol blue and 5% 2-mercaptoethanol. The samples were incubated at 65° C. for 15 min prior to being electrophoresed on a 9% SDS-polyacrylamide gel as above. The primary antibody for detection of PARP (obtained from Enzyme System, Dublin, Calif.) was used at a dilution of 1:5000. Western blotting was carried out as described above.

Immunocytochemistry and TUNEL Staining: For immunostaining, NT2 cells transfected with CLN3 or the vector alone were grown on glass coverslips, and fixed in 2% formaldehyde and 0.2% glutaraldehyde for 15 minutes at 4°

C. NT2 cells stably overexpressing CLN3 were also grown on coverslips and then fixed. The cells were permeabilized by treatment with 0.1% Triton X-100 for 30 minutes at 25° C. followed by incubation in 3% bovine serum albumin (BSA) in phosphate buffered saline (PBS) for 1 hour at 25° C. The cells were then incubated for 16 hours with the CLN3 antibody (IgG fraction) made up in PBS containing 3% BSA. After removal of the primary antibody and washes, the cells were incubated in a 1:500 dilution of biotin conjugated goat-anti-rabbit IgG for 1 hour at 25° C. This was followed by incubation with avidin conjugated horseradish peroxidase for 30 minutes at 25° C. The cells were then washed and incubated with 3,3'-diaminobenzidine (DAB). The cells were counterstained with Hematoxylin Blue, rinsed in xylene and the coverslips mounted on slides. The slides were viewed with a light microscope. TUNEL staining was carried out on transient- or stable-transfected NT2 cells grown on glass coverslips using the fluorescent Apoptag Direct kit (Oncor, Gaithersburg, Md.) following the manufacturer's protocol (Schmitz G *Anal. Biochem.* 192: 222–231 (1991)). After counterstaining with propidium iodide, the coverslips were mounted on slides and the cells visualized under a fluorescent microscope.

Cell proliferation assay by [$^3$H] thymidine incorporation: NT2 cells stably tranfected with CLN3 or the appropriate vector control were plated in 12 well plates at a density of $1\times10^5$ cells/well and incubated with 0.5 µCi/ml [3H] thymidine at the indicated times for 4 h. The cells were then washed twice with ice-cold PBS and the DNA precipitated with 5% trichloroacetic acid. The TCA precipitate was dissolved in 0.4 ml of 0.25 M NaOH and the incorporated [$^3$H] thymidine measured by liquid scintillation counting. For each time point three separate samples were measured.

Ceramide determination: NT2 cells transiently or stably transfected with CLN3 or the vector alone were harvested and the total lipid extracted according to the Bligh & Dyer method (Bligh E G and Dyer W J *Can. J. Biochem. Physiol.* 37: 911–917 (1959)). The ceramide assay was performed as previously described (Zhang J, et al., *Proc. Natl. Acad. Sci. USA.* 93: 5325–5328 (1996)). The labeled ceramide was viewed by autoradiography and quantitated using a liquid scintillation counter. Ceramide was expressed as pmole per nmole of total phospholipid. For measurement of activated ceramide, both the appropriate vector and CLN3-overexpressing cells (transient and stable) were treated with vincristine (1 µg/ml) for 18 h and subjected to lipid extraction followed by ceramide measurements. The data from these experiments is represented as change in ceramide level and reflects the percentage difference in ceramide values before and after vincristine treatment.

II. Results and Discussion

A. Overexpression of CLN3 Increases NT2 Cell Survival

Figure 1A:
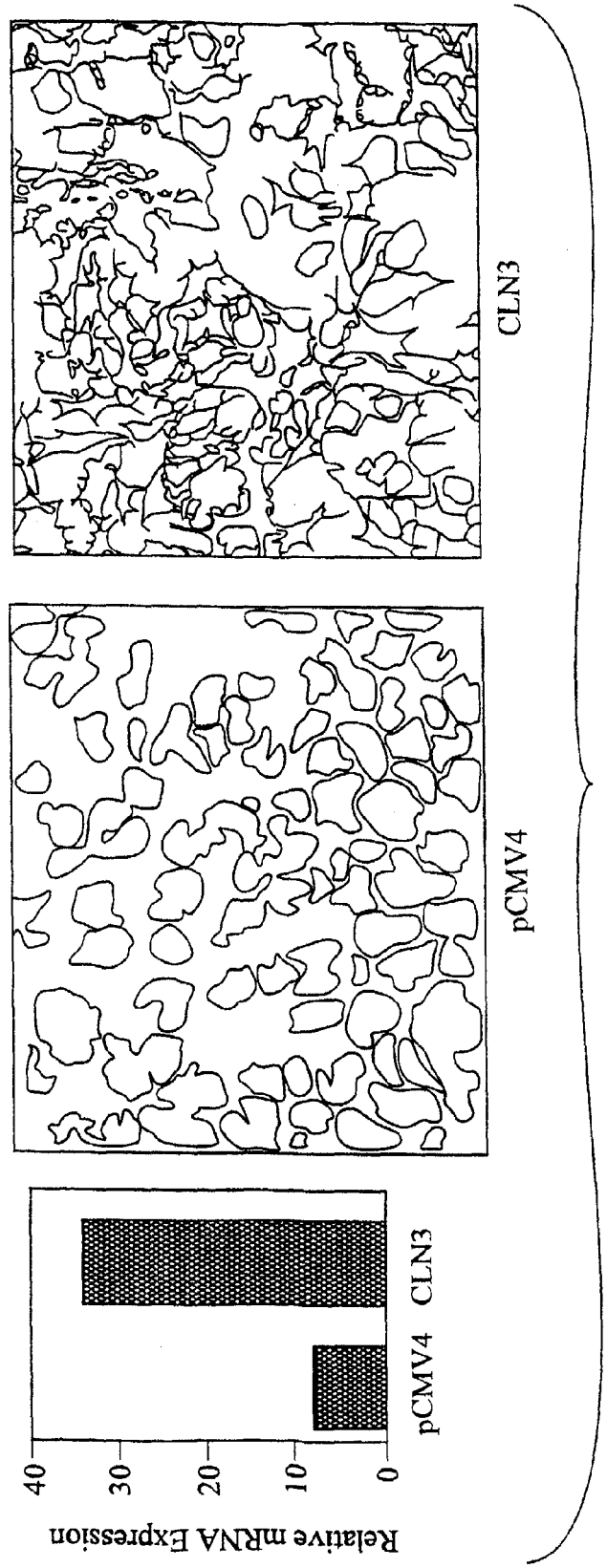
FIG. 1A. Transient overexpression of CLN3: NT2 cells were transiently transfected with CLN3 subcloned into the pCMV4 vector by the calcium phosphate method. The left panel shows results of semi-quantitative RT-PCR analysis expressed as CLN3 mRNA levels relative to the internal control cyclophilin mRNA levels. NT2 cells transfected with 10 µg of CLN3 had a 4.5 times comparatively higher level of CLN3 mRNA than control cells. The right panel shows overexpression of CLN3 at the protein level as determined by immunostaining of NT2 cells with polyclonal anti-CLN3 antibody. Intense brown staining indicates higher levels of CLN3 protein in CLN3 overexpressing compared to control cells (scale bar 5 µm).
Figure 1B:
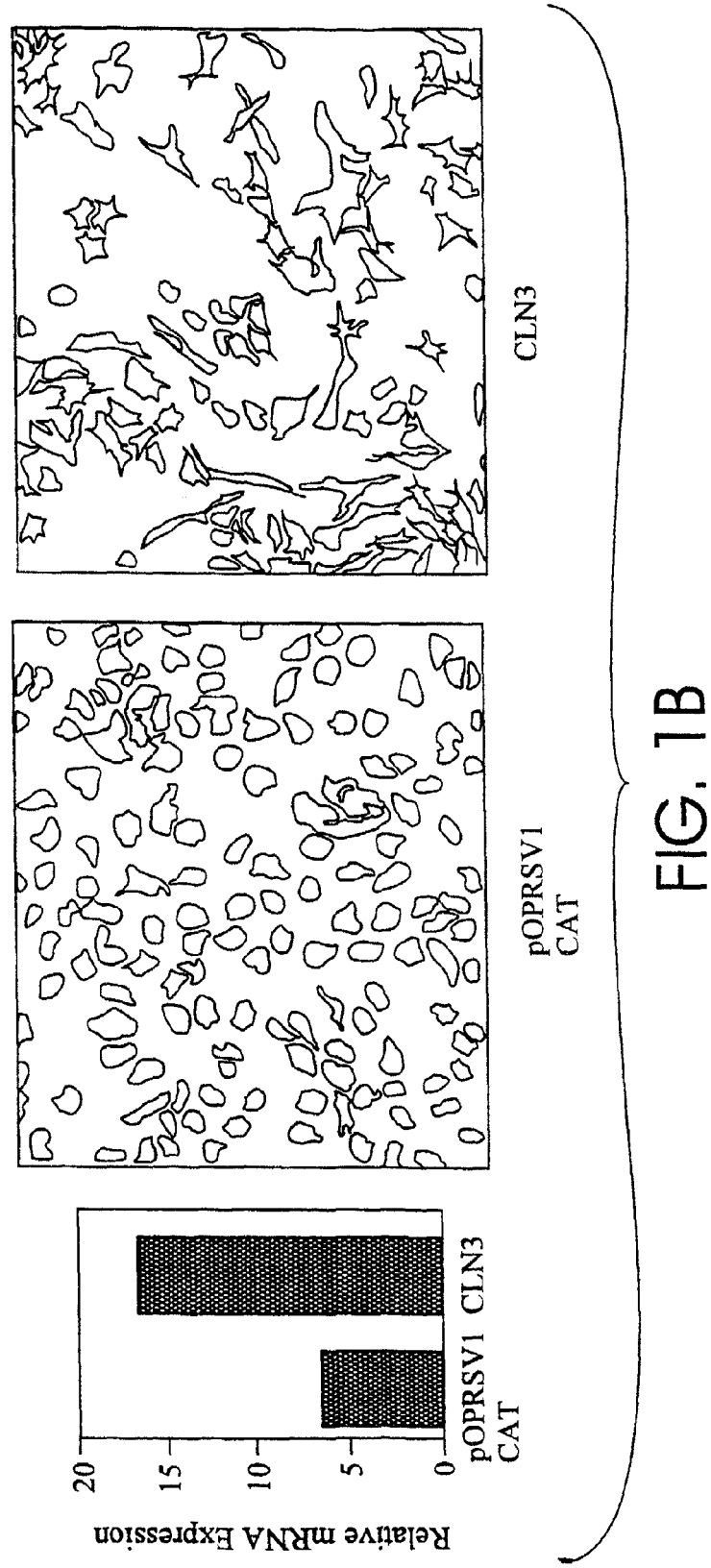
FIG. 1B. Stable overexpression of CLN3: NT2 cells were stably transfected with CLN3 subcloned into the pOPRSV1CAT vector by the calcium phosphate method. RT-PCR analysis shows the stably transfected NT2 cells to have a comparatively 2.5 times higher level of CLN3 mRNA (relative to cyclophilin) with respect to control cells (left panel). The right panel shows overexpression of CLN3 at the protein level as detected by immunostaining.
Figure 1C:
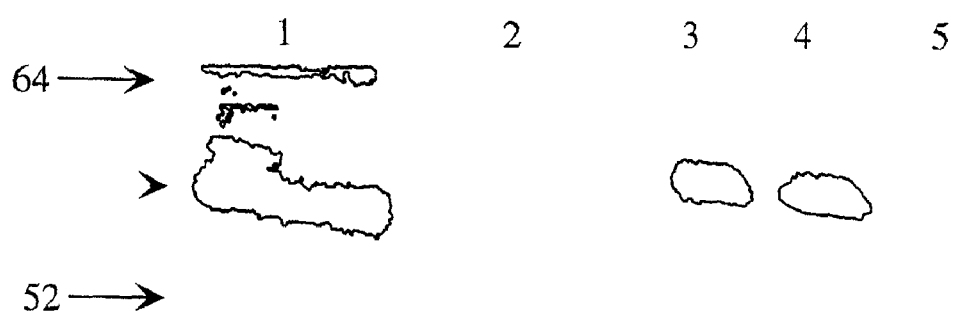
FIG. 1C. Western blot analysis of CLN3 protein overexpression. Equal amounts of protein extracts from NT2 cells overexpressing CLN3 and appropriate controls were analyzed by immunoblotting with anti-CLN3 antibody. Cells were stably transfected with CLN3 subcloned either in the pOPRSV1CAT vector (lane 1) or the pCEP4 vector (lanes 3 and 4). The vector controls are shown in lane 2 (pOPRSV1CAT) and lane 5 (pCEP4). High levels of the CLN3 protein (~55 kDa), indicated by the arrowhead, were observed in all three CLN3 overexpressing cell lines. Molecular weight markers, in kDa, are shown on the left.
Figure 1D:
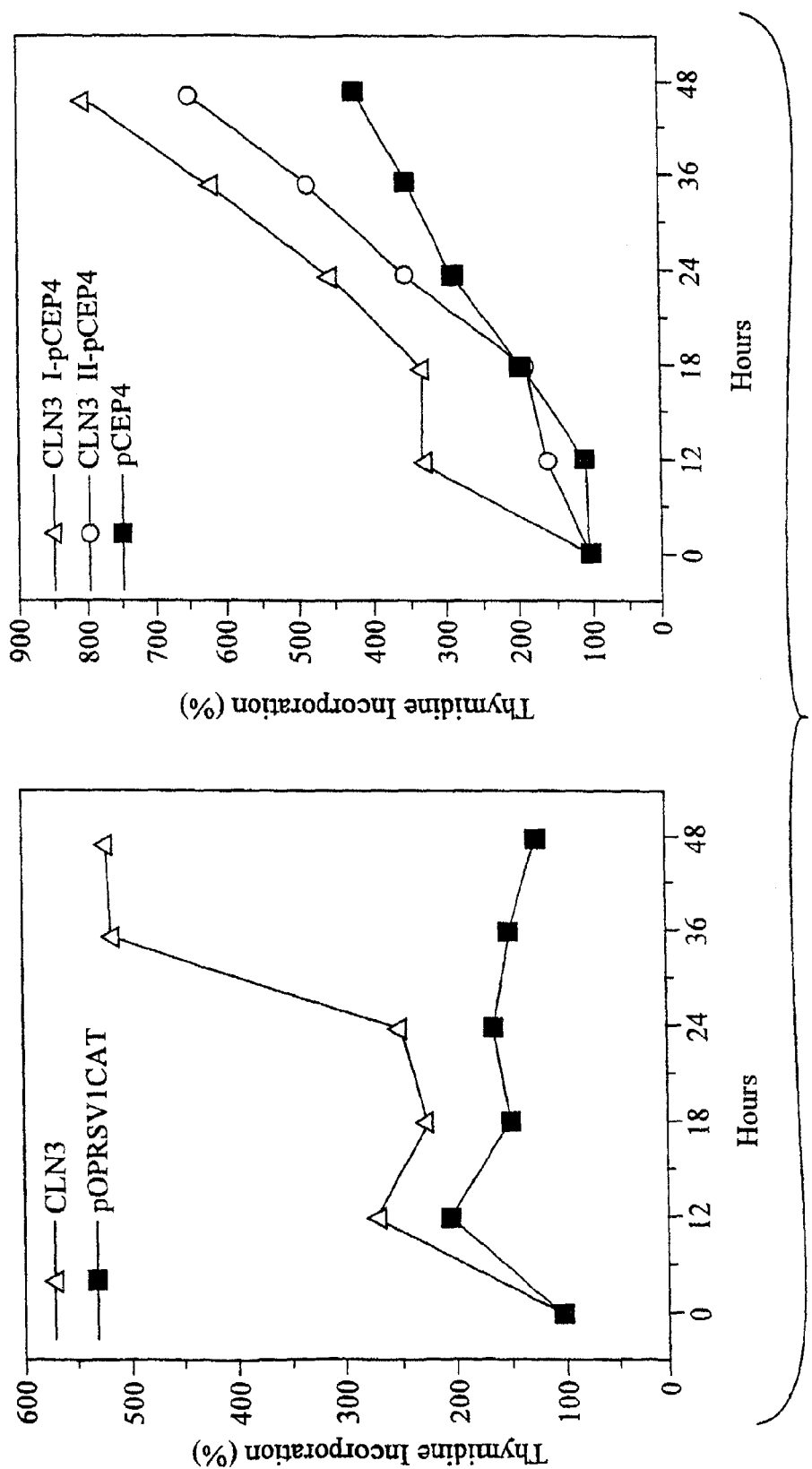
FIG. 1D. Effect of CLN3 overexpression on NT2 cell proliferation: [$^3$H] thymidine was added to NT2 cells stably transfected with CLN3 either in the pOPRSV1CAT vector (left panel) or the pCEP4 vector (right panel) at the indicated times and the incubation continued for another 4 hours. The incorporated [$^3$H] thymidine is represented relative to that at 0 hour which is taken as 100%. Each data point is an average of three samples. The left panel shows results from one stable cell line overexpressing CLN3. The right panel shows results from two additional stable cell lines overexpressing CLN3 (CLN3 I-pCEP4 and CLN3 II-pCEP4).

Transient overexpression of CLN3 subcloned into the pCMV4 vector in NT2 cells was assessed by RT-PCR as shown in the left panel of FIG. 1A. NT2 cells were stably transfected with CLN3 subcloned into pOPRSV1CAT, which resulted in a CLN3 signal 2.5 times stronger in CLN3 transfected NT2 cells compared to vector transfected cells as determined by RT-PCR (FIG. 1B, left panel). CLN3 protein overexpression was demonstrated by Western blot and immunocytochemistry. The Western blot shows that CLN3 protein is expressed at a higher level in three stable NT2 cell clones (CLN3-pOPRSV1CAT seen in FIG. 1D left panel, and CLN3 I-pCEP4 and CLN3 II-pCEP4 seen in FIG. 1D left panel) overexpressing CLN3 in comparison to those transfected with vector alone (FIG. 1C). Immunocytemistry confirms CLN3 overexpression in both a transient overexpression system (FIG. 1A, right panel) and a stable overexpression system (FIG. 1B, right panel). Three different stable NT2 cell clones overexpressing CLN3 had a higher rate of thymidine incorporation compared to corresponding vector controls: for the CLN3-pOPRSV1CAT it was double, and for both pCEP4 clones it was five-fold at 36 h compared to the vector controls. This exceeded 100% at 36 hours for all three clones. This indicates that CLN3 positively modulates the rate of growth of NT2 cells.

B. CLN3 Rescues from Serum Withdrawal Induced Growth Inhibition

Figure 2A:
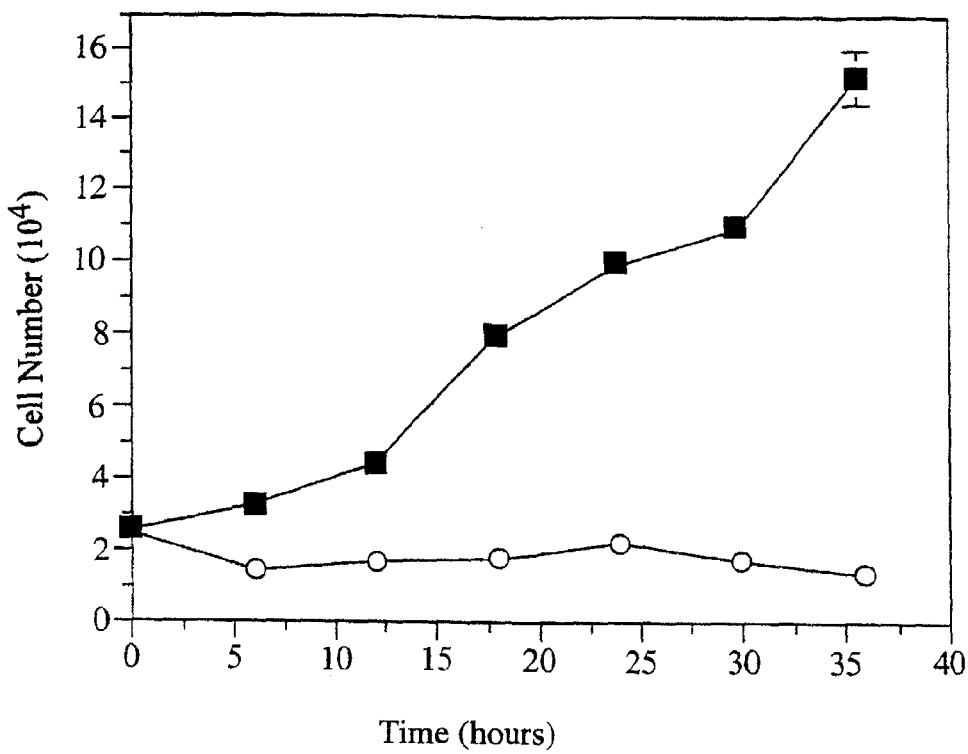
FIG. 2A. Serum deprivation results in inhibition of NT2 cell growth. The rate of growth of NT2 cells in the presence of serum (open square) or absence of serum (open circle) was compared by plating equal numbers of cells and counting at 6, 12, 18, 24 and 36 hours using the trypan blue method.
Figure 2B:
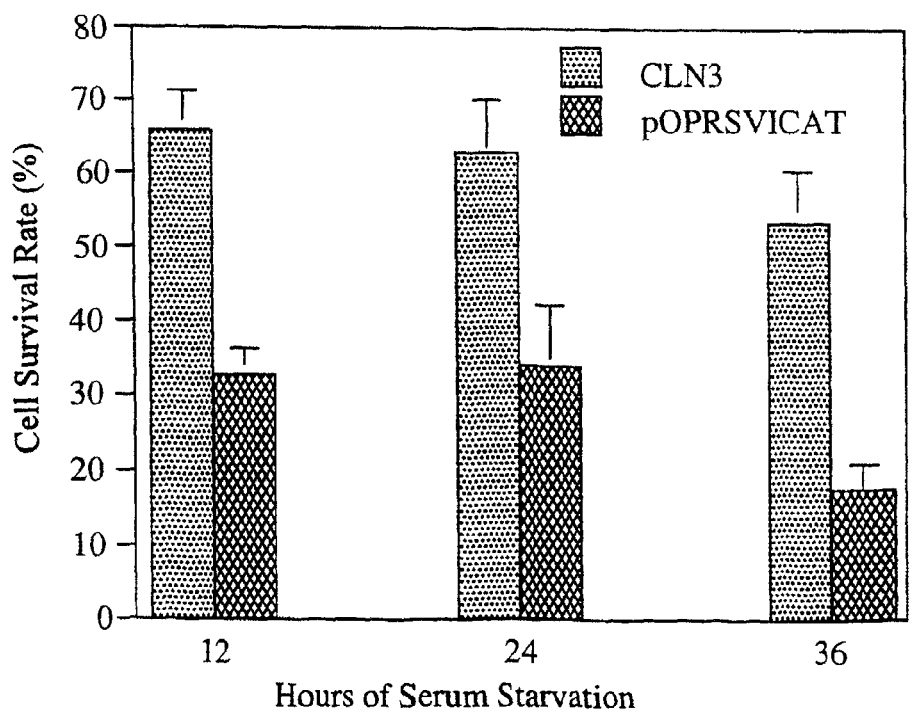
FIG. 2B. CLN3 overexpression enhances the survival of NT2 cells following serum withdrawal. NT2 cells stably transfected with CLN3 or the vector (pOPRSV1CAT) alone were grown in serum free media for 12, 24 and 36 hours and their viability assessed by the trypan blue method. Results are expressed as cell survival rate, which is the ratio of viable cells in serum free media to those in media with serum. Each point is an average of two experiments each of which was carried out in triplicate (p<0.05).

Serum deprivation is known to induce apoptosis in lymphoid (Obeid L M, et al., *Science* 259: 1769–1771 (1993)), neuronal and other cell lines (Howard M K, et al., *J. Neurochem.* 60: 1783–1791 (1993); Kulkarni G V and McCulloch C A *J. Cell Sci.* 107: 1169–1179 (1994)). At the very least serum starvation inhibits growth. We demonstrate that serum starvation induces growth arrest in NT2 cells. NT2 cells grown in DMEM with 10% FBS exhibit logarithmic growth for 38 hours with a doubling time of 14 hours; serum withdrawal blunts logarithmic growth of NT2 cells (FIG. 2A). The effect of stable CLN3 overexpression on growth inhibition induced by serum withdrawal was assessed using the trypan blue dye exclusion method. The survival rate was calculated as the number of viable cells grown in serum free medium divided by the number of viable cells grown in serum supplemented medium. The amount of protection consisted of the difference between survival rate of CLN3- and vector-overexpressing NT2 cells. The degree of protection consists of the amount of protection divided by the survival rate of the vector control cells. CLN3 stably transacted NT2 cells grown in medium lacking serum had a much higher survival rate as compared to NT2 cells stably transfected with vector alone. The degree of protection from serum starvation induced growth inhibition exceeded 100% in cells stably overexpressing CLN3 at 12 hours and was even higher at 36 hours (FIG. 2B).

C. CLN3 Protects from Drug Mediated Apoptosis

The drugs etoposide and vincristine are chemotherapeutic agents known to induce apoptosis. The effect of etoposide is mediated by blocking topoisomerase II (Walker P R, et al., *Cancer Res.* 51: 1078–1085 (1991)), whereas vincristine induces cell death by interfering with spindle formation and the progression of the cell cycle (Harmon B V et al., *Cell Prolif.* 25: 523–536 (1992)). NT2 cells were stably transfected with CLN3 or vector alone followed by treatment with 10 µg/ml of etoposide or 1 µg/ml of vincristine, which are the doses resulting in 50% killing at 18 hours (FIGS. 3Ai and 3Bi). The protection conferred by stable CLN3 overexpression on NT2 cell viability was measured by trypan blue exclusion: CLN3-overexpressing NT2 cells had a degree of protection from cell death exceeding up to 78% following treatment with etoposide (FIG. 3Aii). After vincristine treatment, stable CLN3-overexpressing NT2 cells had up to a 52% degree of protection as compared to vector transfected cells (FIG. 3Bii). Transiently transfected NT2 cells were harvested after 18 hours of drug treatment with etoposide, and stained by the TUNEL technique (data not shown). A much larger number of green apoptotic nuclei is seen in the treated vector cells. Conversely, transient overexpression of antisense CLN3 cDNA decreased the survival rate of NT2 cells treated with etoposide by 10% and vincristine by 16%. Staurosporine, a potent protein kinase inhibitor, has been shown to trigger both the morphological changes and DNA fragmentation associated with apoptosis in many different cell lines (Bertand R, et al., *Exp. Cell Res.* 211: 314–321 (1994)). The optimal staurosporine concentration for causing apoptosis in NT2 cells was established as being 500 nM (FIG. 3Ci). Viability was determined in NT2 cells stably transfected with CLN3 or vector following treatment with 500 nM staurosporine for 18 hours (FIG. 3Cii). The degree of protection of stable CLN3-overexpressing NT2 cell clones ranged from 42% to 129% compared to the corresponding vector-transfected NT2 cells.

Figure 4:
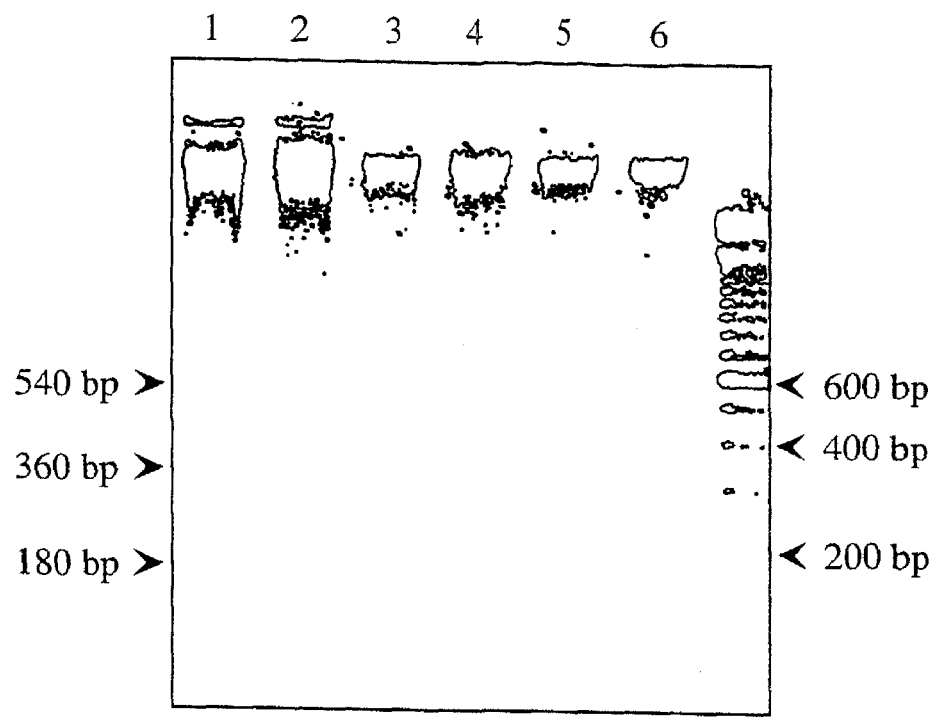
FIG. 4. CLN3 overexpressing NT2 cells show less DNA fragmentation than vector control NT2 cells in response to treatment with etoposide, staurosporine and vincristine. NT2 cells were transiently transfected with CLN3 (lanes 1, 3 and 5) or vector alone (lanes 2, 4 and 6) followed by treatment with either 10 µg/ml etoposide (lanes 1 and 2) or 500 nM staurosporine (lanes 3 and 4) or 1 µg/ml vincristine (lanes 5 and 6). Low molecular weight DNA was extracted and analyzed on a 2% agarose gel in Tris-Borate-EDTA buffer (Rosenbaum et al, *Ann. Neurol.* 36, 864–870 (1994)).

A hallmark of apoptosis is the fragmentation of nuclear DNA into nucleosome-sized fragments creating a DNA ladder of 180 bp and its concatamers (Arends M J, et al., *Am. J. Pathol.* 136: 593–608 (1990)). The drugs etoposide, staurosporine and vincristine cause DNA fragmentation in NT2 cells. NT2 cells were transiently transfected with CLN3 or vector alone, then treated with the drugs prior to the extraction of low molecular weight DNA (Rosenbaum D M, et al., *Ann. Neurol.* 36: 864–870 (1994)). Transient overexpression of CLN3 resulted in a reduction in the extent of DNA fragmentation caused by these drugs (FIG. 4). CLN3 was also found to be protective against vincristine and/or etoposide induced apoptosis in PC-12 neuronal cells, 293 kidney epithelial cells and U937 lymphoid cells. This was seen by either the TUNEL method or DNA ladder formation (results not shown).

D. The Biologic Function of CLN3

These findings assign a major biologic function to the novel gene CLN3 found to be defective in the juvenile form of Batten disease. When overexpressed, CLN3 protects cells from growth arrest induced by serum starvation and from death induced by treatment with the proapoptotic agents vincristine, etoposide and staurosporine. The protective function of CLN3 appears to be vital for maintenance of cell survival in the central nervous system. The evidence for massive and progressive loss of neurons and photoreceptors in patients homozygous for the 1.02 kb CLN3 deletion provides a naturally occurring model where both alleles are knocked out. The neuropathologic lesion in the juvenile form of Batten disease underscores the importance of the CLN3 protein for survival of both neurons and photoreceptor cells. However, we show that the antiapoptotic effect of CLN3 is not just restricted to neurons but is operative in other mammalian cells. We have confirmed it in pheochromocytoma derived PC-12 cells, epithelial 293 cells and lymphoid U937 cells. CLN3 seems to be crucial for the survival of postmitotic, fully differentiated nondividing cells, particularly cortical neurons in the brain and photoreceptor cells in the eye. One possible explanation for this is that the eye and the brain are both immune-privileged sites that cannot tolerate destructive inflammatory responses: Fas—Fas ligand interactions in the eye and brain promote apoptosis and normally protect these organs from tissue damage induced by inflammation (Griffith T S, et al., *Science* 270: 1189–1192 (1995); Griffith T S, et al., *Immunity* 5: 7–16 (1996)). Both neurons and photoreceptors are known to express Fas ligand and lymphoid cells express Fas receptor. This could be one of multiple mechanisms of immune privilege and the reason why loss of function of the antiapoptotic gene, CLN3, is phenotypically expressed only in the eye and brain in Batten disease. The absence or defects in key locations of the CLN3 gene in juvenile Batten may be sufficient for the apoptotic demise of both neurons and photoreceptors.

E. Modulation of Endogenous Ceramide by CLN3

Elevation of proapoptotic ceramide levels in the brain of patients with JNCL suggested a possible link between CLN3 and ceramide (Puranam K, et al., *Neuropediatrics* 28: 37–41 (1997)). We have shown that ceramide levels when measured as pmoles/nmoles of phospholipid drop by 18% in NT2 cells transiently transfected with CLN3 compared to NT2 cells just transfected with vector (FIG. 5A, left panel). Endogenous ceramide levels in NT2 cells stably transfected with CLN3 dropped by 69% (FIG. 5A, right panel). Also, both transient and stable overexpression of CLN3 prevented vincristine-induced activation of ceramide in NT2 cells (FIG. 5B). The attenuation of vincristine-induced activation of ceramide by CLN3 parallels the protective effect of CLN3 overexpression on NT2 cell survival seen following treatment with vincristine (FIG. 3Bii). We show that $C_2$-ceramide is an effective apoptotic agent in NT2 cells (FIG. 5C). Overexpression of CLN3 did not rescue NT2 cells from exogenous ceramide-induced killing (FIG. 5D). This suggests that CLN3 inhibits apoptosis proximally at the level of ceramide signaling in NT2 cells. The proteolytic cleavage of PARP or poly (ADP-ribose) polymerase by the protease caspase-3 has been identified as one of the key downstream events in the execution of apoptotic cell death (White E *Genes Develop*, 10:1–15 (1996)). The chemotherapeutic drug etoposide has been shown to act via this pathway and cause proteolysis of the 116 kDa PARP protein to fragments that are 85 kDa and 25 kDa in size (Kaufmann S, et al., *Cancer Res.* 53: 3976–3985 (1993)). In order to investigate whether CLN3 protection is conferred along this pathway, we studied the effect of overexpression of CLN3 on the cleavage of PARP in NT2 cells. NT2 cells were transiently transfected with CLN3 or vector alone and subsequently treated with 10 μg/ml etoposide for 18 hours. Total cellular extracts were analyzed using a polyclonal anti-PARP antibody by Western blotting (FIG. 6). In the absence of etoposide, the 116 kDa PARP protein is intact in both CLN3 and vector transfected cells. Following etoposide treatment, NT2 cells transiently overexpressing CLN3 show a decrease in the amount of cleaved 85 kDa PARP fragment as compared to control cells. This indicates that CLN3 modulates ceramide levels which in turn lead to a blunting of the activation of the executionary phase of apoptosis by indirectly inhibiting activation of caspase-3, the enzyme that cleaves PARP into the apoptosis specific 85 kDa fragment.

F. Mechanism of Action of CLN3 on Cell Survival

Without wishing to be bound to any particular theory for the instant invention, the following observations are offered. Antiapoptotic agents may protect the cell via one or more of the following: antioxidant effects; regulation of calcium transport; inhibition of the protease cascade; interference with protein translocation, ubiquination or degradation; modulation of signal transduction pathways and/or regulation of release of mitochondrial cytochrome c oxidase (White E *Genes Develop.* 10: 1–15 (1996); Hannun Y A *Science* 274: 1855–1859 (1996); Liu X, et al., *Cell* 86: 147–157 (1996)). The coexistence of elevation of proapoptotic ceramide and apoptosis in brain from patients with JNCL (Lane S C, et al., *J. Neurochem.* 67: 677–683 (1996); Puranam K, et al., *Neuropediatrics* 28: 37–41 (1997)) led us to suggest the following: the signaling lipid second messenger ceramide and the neuroprotective protein CLN3 partake in the same pathway of cell growth and regulation. Significant drops in endogenous and vincristine-activated ceramide levels in response to overexpression of the CLN3 protein in NT2 cells strongly supports this hypothesis. Ceramide formation or breakdown in the cell has at least five, if not more, known origins: 1) sphingomyelin hydrolysis via neutral or acid sphingomyelinase (Rena L A, et al., *Biochem. Pharm.*

53: 615–621 (1997)); 2) breakdown to sphingosine by ceramidase; 3) generation of cerebrosides via cerebroside synthase, 4) de novo synthesis of ceramide by ceramide synthase, and 5) formation of ceramide phosphate by ceramide kinase. CLN3, predicted to reside in the membrane, probably fine-tunes regulation of the apoptotic pathway by blunting or attenuating ceramide generation. CLN3 could be acting as a dimmer-switch for one of the reactions responsible for ceramide formation. One of these enzymes could be a target for the action of the CLN3 protein, or CLN3 could actually be one of those enzymes (FIG. 7). Ceramide leads to activation of caspase-3 (Smyth M J, et al., *Biochem. J.* 316: 25–28 (1996)). We have also shown that the overexpression of CLN3 inhibits the activation of caspase-3 following etoposide treatment as demonstrated in FIG. 7. This occurs probably because CLN3 modulates endogenous ceramide levels further upstream and is most likely not a direct effect of CLN3 on caspase-3. The fact that CLN3 overexpression does not rescue NT2 cells from killing in response to exogenous $C_2$–C6-ceramide confirms that CLN3 is acting upstream of ceramide in the apoptotic pathway. Once killing of cells has been set in motion by exogenously supplied ceramide, CLN3 is impotent in blocking cell death (FIG. 8). This is in contrast to Bcl-2, which acts downstream of ceramide, but upstream of caspase-3 (Perry D K, et al., *Cell Death Differen.* 4: 29–33 (1997); Zhang J, et al., *Proc. Natl. Acad. Sci. U.S.A.* 93: 5325–5328 (1996)). The upregulation of Bcl-2 in surviving neurons from brains of Batten patients actually implies the following: Bcl-2 and CLN3 protect neurons from apoptosis via two separate mechanisms that probably operate independently of one another (Puranam et al, supra). In our hands, PKC α is the predominant form of protein kinase C in NT2 cells. We found no effect of stable CLN3 overexpression on translocation of PKC α in NT2 cells upon stimulation with phorbol esters (0.1 µM PMA) even after 2 hours of stimulation (Lee J Y, et al., *J. Biol. Chem.* 271: 13169–13174 (1996)). Also, stable CLN3 overexpression had no effect on basal or calcium and lipid stimulated PKC kinase activity (unpublished data). This suggests that the effect of CLN3 on ceramide generation and ceramide-induced apoptosis in NT2 cells is independent of PKC signal transduction pathways identifying an alternate route of sphingomyelin signal transduction.

Example 2

CLN3 is Overexpressed in Cancer Cells

I. Materials and Methods

Cell Culture. All cells used are human cell lines. The EB-virus transformed lymphoblast cell line, HS, was grown in suspension in RPMI 1640 media supplemented with 10% fetal bovine serum (FBS). 293 (ATCC #CRL-1573), a kidney epithelial cell line, was grown in Dulbecco's Modified Eagle's Medium (DMEM) supplemented with 10% FBS. The following cell lines were obtained from the American Type Culture Collection (Rockville, Md.). HL-60 cells (ATCC #CCL-240) were grown in RPMI 1640 supplemented with 15% FBS. BT-20 cells (ATCC# HTB-19) were grown in RPMI 1640 supplemented with 5% FBS. BT-474 cells (ATCC # HTB-121) were grown in RPMI 1640 with Insulin and L-Glutamine supplemented with 10% FBS. BT-549 cells (ATCC # HTB-122) were grown in ROMI 1640 supplemented with 10% FBS. HCT-116 cells (ATCC # CCL-247) were grown in McCoy's 5A medium supplemented with 10% FBS. SW1116 (ATCC # CCL-233) and SW480 (ATCC # CCL-288) were both grown in Leibovitz's L-15 medium supplemented with 10% FBS. Hs 683 cells (ATCC # HTB-138), A-172 cells (ATCC # CRL-1620), and A-375 cells (ATCC # CRL-1619) were grown in DMEM supplemented with 10% FBS. IMR-32 cells (ATCC # CCL-127) and C32 cells (ATCC # 1585) were both grown in Eagle's Minimum Essential Medium with non-essential amino acids supplemented with 10% FBS.

All cell lines were supplemented with 100 units each of penicillin and streptomycin and maintained at 37% C in a 5% $CO_2$ atmosphere with the exception of SW1116, which required a free gas exchange environment of $CO_2$ and atmospheric air. Cells were fed 2–3 times/week.

Quantitative RT-PCR. RT-PCR was used to assess differences in CLN3 messenger RNA levels in cell lines. Approximately $2.5 \times 10^5$ cells were used per sample for the mRNA harvesting. The mRNA was isolated from each sample by the oligo-dT-cellulose method using the Quick Prep Micro mRNA Purification kit (Pharmacia Fine Chemicals, Piscataway, N.J.). The mRNA was then converted to cDNA by the reverse transcription (RT) reaction in accordance with known techniques. For each sample, one-fourth of the RNA obtained, or 5 µl, was used for the RT reaction. The RT reaction was carried out in buffer containing 50 mM Tris-HCL, pH 8.3, 40 mM KCL, 6 mM $MgCl_2$, 1 mM DTT, 0.5 mM each of dATP, dCTP, dGTP and dTTP, 16 µM random primers (haxamers) and 20 U Rnasin (Promega Corp., Madison, Wis.) in a final volume of 30 µl. After addition of 1 U of Superscript reverse transcriptase (GIBCO BRL), the sample was incubated at 20° C. for 10 minutes followed by 50 minutes at 42° C. The reaction was terminated by adding 70 µl DEPC treated water and incubating at 94° C. for 5 minutes. The PCR reactions were set up with 10 µl of the cDNA, synthesized in the RT reaction above, 1 U of Taq polymerase (Perkin Elmer), and 5 µCi of $\alpha^{32}$P-dCTP in each reaction. The reactions were performed in Taq buffer (Perkin Elmer), containing 15. mM $MgCl_2$, 2.5 mM dCTP and 5 mM each of dATP, dGTP, and dTTP. The primers use for amplification of CLN3 and cyclophilin, an internal control for mRNA, are listed below. The reaction conditions used for amplification were 1 minute at 94° C., 1 minute at 50° C., and 2 minutes at 72° C. for 20 cycles in a 9600 Perkin Elmer Thermocycler (Foster City, Calif.). The PCR amplified products were analyzed on an 8% nondenaturing acrylamide gel, which as dried and visualized by autoradiography. The amplified signal was quantitated on a Molecular Dynamics phosphorimager using ImageQuant software (Sunnyvale, Calif.). The results are expressed as the ratio of CLN3 signal to that of the internal control, cyclophilin; the quantitated value of CLN3 present in the sample was divided by the quantitated value of cyclophilin.

Primers used for PCR amplification of human CLN3 were:

5' primer: 5'-GGTGGACAGTATTCAGGG-3' (958–976, SEQ ID NO: 1)

3' primer: 5'-CTTGGCAGAAAGACGAAC-3' (1229–1246, SEQ ID NO: 2)

Primers used for amplification of human cyclophilin amplification:

5' primer: 5'-AAATGCTGGACCCAACAC-3' (317–334, SEQ ID NO: 3)

3' primer: 5'-AAACACCACATGCTTGCC-3' (384–401, SEQ ID NO: 4)

II. Results.

An initial look at EB-virus transformed lymphoblasts (HS) and a leukemia cell line (HL-60) show that HL-60 cells had 2.3 times more CLN3 expression than HS after normalizing to the internal control, cyclophilin (FIG. 8A). Next, 293, a kidney epithelial cell line, was chosen as a control because a wide variety of cancer cell morphology is epithelial. To test its suitability and viability as a control, the level of CLN3 expressed in 293 was compared to the levels expressed in HCT-116, a colon cancer cell line, and BT-20, a breast cancer cell line. CLN3 levels were 4.1 and 2.8 times more in HCT-116 and BT-20, respectively, than in 293 (FIG. 9A).

Based on the elevated CLN3 expression of BT-20 compared to 293, two more breast cancer cell lines, BT-474 and BT-549, were selected for comparison with 293 along with BT-20. Results show that all three breast cancer cells have upregulated CLN3 mRNA levels compared to 293 (FIG. 10A). BT-474, BT-20, and BT-549 had 1.9, 3.0, and 4.8 times more CLN3 expression than 293, respectively. To better substantiate the elevated CLN3 expression in HCT-116, a well differentiated colon cancer cell line, SW480, and a poorly differentiated colon cancer cell line, SW1116, were chosen, along with HCT-116, for comparison with 293 (FIG. 11A). HCT-116 again showed over-expression of CLN3 compared to 293, with 3.0 times more CLN3 expressed. SW480 showed a more dramatic over-expression, with 7.7 times the level of 293. SW1116 had the largest difference in CLN3 expression compared to 293, with 21.5 times more CLN3 expressed.

A further screening of other cancer types was conducted. Two melanoma cell lines, C32 and A-375, a neuroblastoma cell line, IMR-32, a glioma cell line, Hs683, and a glioblastoma cell line, A-172, were compared against 293 (FIG. 12A). Interestingly, C32 (melanoma) actually showed 0.8 times the CLN3 expression compared to 293. It was the only cell line examined in this experiment that had less CLN3 expression than 293. The other melanoma cell line, A-375, and the glioblastoma cell line A-172, both had a very slight upregulation of CLN3, with 1.2 times more than 293. Hs683, the glioma cell line, had 1.7 times the CLN3 expression compared to 293. The neuroblastoma cell line, IMR-32, had a notable 12.7 times the CLN3 expression compared to 293.

Example 3

Preparation of Adenoviral CLN3 Antisense Vectors

A CMV enhancer/promoter element, juxtaposed to the CLN3 DNA in an antisense configuration, followed by the SV-40 polyadenylation signal was subcloned as a minigene cassette into the AscI site of the shuttling plasmid pAdAscLwt. PAdAscLwt contains as a circular plasmid: nucleotides 1–358 of the Ad5 genome, followed by the AscI restriction enzyme subcloning site, followed by nucleotides 3329–15671 of the Ad5 genome, followed by the bacterial plasmid backbone containing the ampicillin resistance gene and bacterial origin of replication derived from the commonly used bacterial plasmid pAT153. The resultant plasmid was designated pAdAscLwtCMV-antisenseCLN3pA. The shuttle plasmid was linearized by restriction enzyme digestion, and contransfected into human 293 cells (supplying adenoviral E1 functions in trans) along with ClaI restriction enzyme digested full length adenoviral DNA. Successful recombination between the homologous portions of the shuttle plasmid and the Ad viral DNA sequences resulted in the generation of a recombinant, E1 deleted Ad vector capable of transducing the CMV-driven antisense CLN3 cDNA to all cells amenable to Ad vector infection.

Example 4

CLN3 Antisense Vectors Inhibit Growth of Cancer Cells

Cell proliferation was assayed by counting cell numbers and measuring [$^3$H]-thymidine incorporation. Data were expressed as the mean values of three wells.

To observe a dose-response relationship, BT-20 breast cancer cells and SW1116 colon cancer cells were plated overnight in 24-well plates at a density of $1\times10^5$ cells/well. Then, cells were infected with Ad-Antisense-CLN3 or adenovirus (vector) at 8, 40, and 80 MOI. After 24 hours, 0.5 µCi/ml [$^3$H]thymidine (DuPont) was added to each well for 4 hours. To measure [$^3$H]thymidine incorporation, each well was washed with two changes of ice-cold PBS. Thereafter, DNA was precipitated with 5% trichloroacetic acid and dissolved in 0.4 ml of 0.25 M NaOh. Incorporated radioactivity was detected by liquid scintillation counting. Data for SW116 is given in FIG. 13.

To study a time-response relationship, BT-20 and SW1116 cells were plated overnight in 12 well plates at a density of $2\times10^5$ cells/well. Then, cells were infected with Ad-Antisense-CLN3 or adenovirus (vector) at 10 MOI. At the indicated dates, cell prolilferation was assayed by [$^3$H] thymidine incorporation and/or by counting cells using a hemocytometer. Cell growth of SW116 after one-day infection is given as thymidine uptake in FIG. 14 and as cell numbers at various days after infection in FIG. 15. Cell growth of BT-20 cells after one-day infection is given in FIG. 16, and as cell numbers at various days after infection in FIG. 17. Finally, thymidine uptake of BT-20 cells at various days after infection is given in FIG. 18.

These data indicate that the proliferation of cancer cells, specifically colon cancer cells and breast cancer cells, is inhibited by infection with a vector that expresses an antisense construct to the CLN3 gene transcript.

The foregoing is illustrative of the present invention, and is not to be construed as limiting thereof. The invention is defined by the following claims, with equivalents of the claims to be included therein.

What is claimed is:

1. A method of identifying a human subject having an increased risk of developing colon cancer, comprising detecting upregulation of the CLN3 gene in said subject, wherein upregulation of the CLN3 gene in said subject identifies the subject as having an increased risk of developing colon cancer.

2. The method of claim 1, wherein said subject has been previously diagnosed with colon cancer.

3. The method of claim 1, wherein said subject has not been previously diagnosed with colon cancer.

4. The method of claim 1, wherein said subject has been previously identified to be at increased risk of developing colon cancer.

5. The method of claim 1, wherein said subject has not been previously identified to be at increased risk of developing colon cancer.

6. The method of claim 1, wherein said detecting step is carried out by detecting increased mRNA levels for said CLN3 gene.

7. The method of claim 1, wherein said subject has undergone treatment for colon cancer.

* * * * *

SEQUENCE LISTING

<160> NUMBER OF SEQ ID NOS: 5

<210> SEQ ID NO 1
<211> LENGTH: 19
<212> TYPE: DNA
<213> ORGANISM: Artificial sequence
<220> FEATURE:
<223> OTHER INFORMATION: Synthetic oligonucleotide

```
<400> SEQUENCE: 1
ggtggacagt attcaaggg                                              19

<210> SEQ ID NO 2
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 2
cttggcagaa agacgaac                                               18

<210> SEQ ID NO 3
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 3
aaatgctgga cccaacac                                               18

<210> SEQ ID NO 4
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 4
aaacaccaca tgcttgcc                                               18

<210> SEQ ID NO 5
<211> LENGTH: 20
<212> TYPE: PRT
<213> ORGANISM: Artificial sequence
<220> FEATURE:
<223> OTHER INFORMATION: Synthetic polypeptide

<400> SEQUENCE: 5

Ala Ala His Asp Ile Leu Ser His Lys Arg Thr Ser Gly Asn Gln Ser
1               5                   10                  15

His Val Asp Pro
            20
```